(12) United States Patent
Siemionow

(10) Patent No.: US 12,337,015 B2
(45) Date of Patent: Jun. 24, 2025

(54) MYOBLAST CHIMERIC CELLS (MCCs)

(71) Applicant: Dystrogen Therapeutics Corporation, Chicago, IL (US)

(72) Inventor: Maria Siemionow, Chicago, IL (US)

(73) Assignee: DYSTROGEN THERAPEUTICS CORPORATION, Chicago, IL (US)

( * ) Notice: Subject to any disclaimer, the term of this patent is extended or adjusted under 35 U.S.C. 154(b) by 943 days.

(21) Appl. No.: 17/439,210

(22) PCT Filed: Mar. 13, 2020

(86) PCT No.: PCT/US2020/022712
§ 371 (c)(1),
(2) Date: Sep. 14, 2021

(87) PCT Pub. No.: WO2020/186197
PCT Pub. Date: Sep. 17, 2020

(65) Prior Publication Data
US 2022/0160783 A1  May 26, 2022

Related U.S. Application Data

(60) Provisional application No. 62/818,435, filed on Mar. 14, 2019.

(51) Int. Cl.
*A61K 35/34* (2015.01)
*C12N 5/077* (2010.01)
*C12N 5/12* (2006.01)

(52) U.S. Cl.
CPC ............ *A61K 35/34* (2013.01); *C12N 5/0658* (2013.01); *C12N 5/12* (2013.01)

(58) Field of Classification Search
CPC .................................................. A61K 35/34
See application file for complete search history.

(56) References Cited

U.S. PATENT DOCUMENTS

| | | |
|---|---|---|
| 2011/0136145 A1 | 6/2011 | Song et al. |
| 2015/0250826 A1 | 9/2015 | Wagers et al. |
| 2018/0221416 A1* | 8/2018 | Siemionow ............ A61K 35/34 |

OTHER PUBLICATIONS

Siemionow et al. "Creation of Dystrophin Expressing Chimeric Cells of Myoblast Origin as a Novel Stem Cell Based Therapy for Duchenne Muscular Dystrophy". Stem Cell Rev Rep. Apr. 2018;14(2):189-199. (Year: 2018).*
Siemionow et al., "Dystrophin Expressing Chimeric (DEC) Human Cells Provide a Potential Therpay for Duchenne Muscular Dystrophy". Stem Cell Rev and Rep 14, 370-384 (2018). (Year: 2018).*
International Search Report and Written Opinion for PCT/US20/22712. Mailed Jul. 28, 2020. 22 pages.
Aebischer et al., Gene therapy for amyotrophic lateral sclerosis (ALS) using a polymer encapsulated xenogenic cell line engineered to secrete Hontf. Hum Gene Ther. May 1, 1996;7(7):851-60.
Deglon et al., Central nervous system delivery of recombinant ciliary neurotrophic factor by polymer encapsulated differentiated C2C12 myoblasts. Hum Gene Ther. Nov. 10, 1996;7(17):2135-46.
Siemionow et al., Creation of Dystrophin Expressing Chimeric Cells of Myoblast Origin as a Novel Stem Cell Based Therapy for Duchenne Muscular Dystrophy. Stem Cell Rev Rep. Apr. 2018;14(2):189-199.
Siemionow et al., Dystrophin Expressing Chimeric (DEC) Human Cells Provide a Potential Therapy for Duchenne Muscular Dystrophy. Stem Cell Rev Rep. Jun. 2018;14(3):370-384.
Spinazzola et al., Isolation of Primary Human Skeletal Muscle Cells. Bio Protoc. Nov. 5, 2017;7(21):e2591. 16 pages.
Tresco et al., Polymer encapsulated neurotransmitter secreting cells. Potential treatment for Parkinson's disease. Asaio J. Jan.-Mar. 1992;38(1):17-23.

* cited by examiner

*Primary Examiner* — Allison M Fox
*Assistant Examiner* — Hanan Isam Abuzeineh
(74) *Attorney, Agent, or Firm* — Jason R. Bond; Casimir Jones, S.C.

(57) ABSTRACT

The present invention relates to methods and compositions for generating and using myoblast chimeric cells (MCCs) for treating a muscle disease, such as muscular dystrophy, where the MCCs are composed of a myoblast derived from a patient with muscle disease (MD) and a myoblast from a donor without the MD (e.g., a healthy donor). In certain embodiments, cell fusion methods are performed using 2-4, or 5, times passaged myoblasts from the MD and donor subject, and/or polyethylene glycol 0.5-1.5 g/ml. In other embodiments, the MCCs created by fusion are passaged 1-5 times before use, and are passaged at 60-80% confluency. In further embodiments, the myoblasts and/or MCCs are tested at any stage during the process for less than 5-10% CD34 and/or CD45 expression, and/or greater than 50-70% CD56 and/or CD90 expression.

11 Claims, 12 Drawing Sheets

Exemplary Myoblast Chimeric Cells (MCC) Production Timeline

Exemplary Decision Flowchart for Cryopreservation and Final MCC Product Preparation

MYOBLAST CHIMERIC CELLS (MCCs)

FIELD OF THE INVENTION

The present invention relates to methods and compositions for generating and using myoblast chimeric cells (MCCs) for treating a muscle disease, such as muscular dystrophy, where the MCCs are composed of a myoblast derived from a patient with muscle disease (MD) and a myoblast from a donor without the MD (e.g., a healthy donor). In certain embodiments, cell fusion methods are performed using 2-4 times, or 5 times, passaged myoblasts from the MD and donor subject, and/or polyethylene glycol at 1.0-1.3 g/ml or 0.4-1.5 g/ml (e.g., about 0.65 g/ml). In other embodiments, the MCCs created by fusion are passaged 1-3 or 4-5 times before use, and are passaged at 60-80% confluency. In further embodiments, the myoblasts and/or MCCs are tested at any stage during the process for less than 5-10% CD34 and/or CD45 expression, and/or greater than 50-70% CD56 and/or CD90 expression.

BACKGROUND OF THE INVENTION

Muscular dystrophy is a group of inherited disorders characterized by progressive muscle weakness and loss of muscle tissue. Muscular dystrophies include many inherited disorders, including Becker's muscular dystrophy and Duchenne's muscular dystrophy, which are both caused by mutations in the dystrophin gene. Both of the disorders have similar symptoms, although Becker's muscular dystrophy is a slower progressing form of the disease. Duchenne's muscular dystrophy is a rapidly progressive form of muscular dystrophy.

Both disorders are characterized by progressive muscle weakness of the legs and pelvis which is associated with a loss of muscle mass (wasting). Muscle weakness also occurs in the arms, neck, and other areas, but not as severely as in the lower half of the body. Calf muscles initially enlarge (an attempt by the body to compensate for loss of muscle strength), the enlarged muscle tissue is eventually replaced by fat and connective tissue (pseudohypertrophy). Muscle contractions occur in the legs and heels, causing inability to use the muscles because of shortening of muscle fibers and fibrosis of connective tissue. Bones develop abnormally, causing skeletal deformities of the chest and other areas. Cardiomyopathy occurs in almost all cases. Mental retardation may accompany the disorder but it is not inevitable and does not worsen as the disorder progresses. The cause of this impairment is unknown. Becker's muscular dystrophy occurs in approximately 3 out of 100,000 people. Symptoms usually appear in men between the ages of 7 and 26. Women rarely develop symptoms. There is no known cure for Becker's muscular dystrophy. Treatment is aimed at control of symptoms to maximize the quality of life. Activity is encouraged. Inactivity (such as bed rest) can worsen the muscle disease. Physical therapy may be helpful to maintain muscle strength. Orthopedic appliances such as braces and wheelchairs may improve mobility and self-care. Becker's muscular dystrophy results in slowly progressive disability. A normal life span is possible; however, death usually occurs after age 40.

Duchenne's muscular dystrophy occurs in approximately 2 out of 10,000 people. Symptoms usually appear in males 1 to 6 years old. Females are carriers of the gene for this disorder but rarely develop symptoms. Treatment is aimed at control of symptoms to maximize the quality of life. Activity is encouraged. Inactivity (such as bed rest) can worsen the muscle disease. Physical therapy may be helpful to maintain muscle strength and function. Orthopedic appliances such as braces and wheelchairs may improve mobility and the ability for self-care. Duchenne's muscular dystrophy results in rapidly progressive disability. By age 10, braces may be required for walking, and by age 12, most patients are confined to a wheelchair. Bones develop abnormally, causing skeletal deformities of the chest and other areas. Muscular weakness and skeletal deformities contribute to frequent breathing disorders. Cardiomyopathy occurs in almost all cases. Intellectual impairment is common but is not inevitable and does not worsen as the disorder progresses. Death usually occurs by age 15, typically from respiratory (lung) disorders.

SUMMARY OF THE INVENTION

The present invention relates to methods and compositions for generating and using myoblast chimeric cells (MCCs) for treating a muscle disease, such as muscular dystrophy, where the MCCs are composed of a myoblast derived from a patient with muscle disease (MD) and a myoblast from a donor without the MD (e.g., a healthy donor). In certain embodiments, cell fusion methods are performed using 2-4 times, or 5 times, passaged myoblasts from the MD and donor subject, and/or polyethylene glycol at 0.6-1.5 g/ml or 1.0-1.3 g/ml (e.g., about 0.65 g/ml). In other embodiments, the MCCs created by fusion are passaged 1-3, or 4-5, times before use, and are passaged at 60-80% confluency. In further embodiments, the myoblasts and/or MCCs are tested at any stage during the process for less than 5-10% CD34 and/or CD45 expression, and/or greater than 50-70% or 60-70% CD56 and/or CD90 expression.

In some embodiments, provided herein are methods of generating myoblast chimeric cells comprising: a) establishing: i) a MD (muscle disease) cell culture comprising MD non-passaged myoblast cells derived from a first human subject with a muscle disease (MD), and ii) a Donor cell culture comprising non-passaged Donor myoblast cells derived from a second human subject without said MD; b) culturing and passaging said MD cell culture, and said Donor cell culture, at least twice and not more than four times, to generate: i) a population of 2-4 times (or 5 times) passaged MD myoblasts, and ii) a population of 2-4 times (or 5 times) passaged Donor myoblasts; c) combining at least a portion of said population of 2-4 times (or 5 times) passaged MD myoblasts, with at least a portion of said population of 2-4 times (or 5 times) passaged Donor myoblasts, to generate a cell mixture, and d) adding a cell-fusion solution to said cell mixture to generate a cell fusion reaction such that a population of myoblast chimeric cells (MCCs) is generated, wherein each of said MCCs comprises: i) one of said 2-4 times (or 5 times) passaged MD myoblasts, and ii) one of said 2-4 times (or 5 times) passaged Donor myoblasts.

In certain embodiments, the culturing and passaging of the MD cell culture and the Donor cell culture is performed three times, generating a population of 3 times passaged MD myoblasts and a population of 3 times Donor myoblasts, and wherein each of the MCCs comprise one of the 3 times passaged MD myoblasts and one of the 3 times passaged Donor myoblasts. In other embodiments, the culturing and passaging of MD cell culture is performed three times, and the culturing and passaging of the Donor cell culture is performed four times, generating a population of 3 times passaged MD myoblasts and 4 times Donor myoblasts, and wherein the each of the MCCs comprise one of the 3 times passaged MD myoblasts and one of the 4 times passaged Donor myoblasts. In further embodiments, the culturing and passaging of MD cell culture is performed four times, and the culturing and passaging of the Donor cell culture is performed three times, generating a population of 4 times passaged MD myoblasts and 3 times Donor myoblasts, and wherein the each of the MCCs comprise one of the 4 times passaged MD myoblasts and one of the 3 times passaged Donor myoblasts.

In some embodiments, the methods further comprise testing at least one of the following: the population of 2-4 times (or 5 times) passaged MD myoblasts and the population of 2-4 times (or 5 times) passaged Donor myoblasts, wherein the testing generates at least one tested cell population, and wherein the tested cell population meets at least one (e.g., 1, 2, 3, or all 4) of the following criteria: i) less than 10% of the passaged myoblasts express CD34, ii) less than 10% of the passaged myoblasts express CD45, iii) greater than 45% or 50% or 60% of the passaged myoblasts express CD56, and iv) greater 45% or 50% or 60% than of the passaged myoblasts express CD90. In other embodiments, the tested cell population meets at least one (e.g., 1, 2, 3, or all 4) of the following criteria: i) less than 5% of the passaged myoblasts express CD34, ii) less than 5% of the passaged myoblasts express CD45, iii) greater than 70% of the passaged myoblasts express CD56, and iv) greater than 70% of the passaged myoblasts express CD90.

In certain embodiments, the cell-fusion solution comprises polyethylene glycol (PEG) at a concentration of 1.0-1.3 g/ml or 0.6-1.5 g/ml or 0.5-1.6 g/ml (e.g., 0.5 . . . 0.6 . . . 0.65 . . . 0.7 . . . 1.0 . . . 1.1 . . . 1.2 . . . or 1.5 g/ml). In further embodiments, the methods further comprise: e) culturing and passaging the MCCs at least once and not more than three times, to generate: a population of 1-3 times passaged MCCs. In other embodiments, the passaging of the MCCs at least once but not more than three times is when, for each passaging, the MCCs are at about 60-80% confluency (e.g., 60% . . . 64% . . . 68% . . . 72% . . . 75% . . . or 80%). In other embodiments, the methods further comprise filling a medication vial (such as CellSeal 2 ml or 5 ml) or syringe, with the 1-3, or 4-5, times passaged MCCs, wherein the MCCs are suspended in a carrier liquid (such as sterile saline—0.9% NaCl) at the density of about 20×10$^6$ cells/ml. In additional embodiments, the syringe is configured for intra-bone delivery of the 1-4 or 5 or more times passaged MCCs to a subject. In certain embodiments, the MCCs are mixed with a carrier liquid, such as saline prior to introduction into the vial or syringe. In certain embodiments, the carrier liquid comprises a saline sterile 0.9% NaCl saline solution.

In further embodiments, the methods further comprise: administering the 1-3 or 4-5 or more times passaged MCCs to the first subject with the MD. In additional embodiments, the administering is intra-bone into a bone of the first subject. In other embodiments, the culturing and passaging the MD cell culture, and the Donor cell culture, at least twice and not more than four times, is performed when such cell cultures are at about 60-80% confluency (e.g., 60% . . . 64% . . . 68% . . . 72% . . . 75% . . . or 80%). In some embodiments, the muscle disease (MD) of the first subject is a muscular dystrophy. In certain embodiments, the muscular dystrophy is Duchenne muscular dystrophy.

In some embodiments, provided herein are methods of culturing and passaging myoblast chimeric cells comprising: a) establishing a first cell culture of myoblast chimeric cells (MCCs) in a first container, wherein each of the MCCs comprises: i) a first cultured myoblast cell derived from a first human subject with a muscle disease (MD), and ii) a second cultured myoblast cell derived from a second human subject without the MD; b) culturing the first cell culture in the first container until an expanded about 60-80% confluent first cell culture is established that is adherent and has at least twice as many MCCs as the first cell culture; and c) passaging at least a portion of the expanded about 60-80% confluent first cell culture into a second container such that a second cell culture is established in the second container.

In certain embodiments, the methods further comprise: d) culturing the second cell culture in the second container until an expanded about 60-80% (e.g., 60% . . . 64% . . . 68% . . . 72% . . . 75% . . . or 80%) confluent second cell culture is established that is adherent and has at least twice as many MCCs as the second cell culture. In other embodiments, the methods further comprise: e) testing at least one of the following: the first cell culture, the expanded about 60-80% confluent first cell culture, the second cell culture, and the expanded about 60-80% confluent second cell culture, wherein the testing generates at least one first-tested cell culture, and wherein the first-tested cell culture meets at least one of the following criteria: i) less than 10% of the MCCs in the first-tested cell culture express CD34, ii) less than 10% of the MCCs in the first-tested cell culture express CD45, iii) greater than 60% of the MCCs in the first-tested cell culture express CD56, and iv) greater than 60% of the MCCs in the first-tested cell culture express CD90. In further embodiments, the first-tested cell culture meets at least one of the following criteria: i) less than 5% of the MCCs in the first-tested cell culture express CD34, ii) less than 5% of the MCCs in the first-tested cell culture express CD45, iii) greater than 45% or 70% of the MCCs in the first-tested cell culture express CD56, and iv) greater than 45% or 70% of the MCCs in the first-tested cell culture express CD90.

In additional embodiments, the methods further comprise: e) passaging at least a portion of the expanded about 60-80% confluent second cell culture into a third container such that a third cell culture is established in the third container. In other embodiments, the methods further comprise loading at least a portion of the third cell culture, mixed with a carrier liquid, into a medication vial, or syringe, for human administration. In additional embodiments, the methods further comprise: f) culturing the third cell culture in the third container until an expanded about 60-80% confluent third cell culture is established that is adherent and has at least twice as many MCCs as the third cell culture. In additional embodiments, the methods further comprise: g) testing the third cell culture and/or the expanded about 60-80% confluent third cell culture to generate a second-tested cell culture, and wherein the second-tested cell culture meets at least one of the following criteria: i) less than 10% of the MCCs in the second-tested cell culture express CD34, ii) less than 10% of the MCCs in the second-tested cell culture express CD45, iii) greater than 45% or 50% or 60% of the MCCs in the second-tested cell culture express CD56, and iv) greater than 45% or 50% or 60% of the MCCs in the second-tested cell culture express CD90.

In additional embodiments, wherein the first-tested cell culture meets three or all four of the criteria. In further embodiments, the second-tested cell culture meets at least one of the following criteria: i) less than 5 or 10% of the MCCs in the second-tested cell culture express CD34, ii) less than 5 or 10% of the MCCs in the second-tested cell culture express CD45, iii) greater than 45% or 50% or 70% of the MCCs in the second-tested cell culture express CD56, and iv) greater than 45% or 50% or 70% of the MCCs in the second-tested cell culture express CD90. In other embodiments, the first-tested cell culture meets at least one of the following additional criteria: i) greater than 80% cell viability, ii) greater than 20% or 40% or 60% Desmin (DES) expression, and iii) greater at least 10% Dystrophin expression as compared to a cultured myoblast dystrophin expression (e.g., at least 10% . . . 30% . . . 40% . . . 45% . . . or 50% expression).

In additional embodiments, the methods further comprise loading the second cell culture, mixed with a carrier liquid at the density of about $20 \times 10^6$ cells/ml (e.g., plus or minus 5% or 10%), into a medication vial, or syringe, for human administration. In additional embodiments, the muscle disease (MD) of the first subject is a muscular dystrophy. In further embodiments, the muscular dystrophy is Duchenne muscular dystrophy. In some embodiments, the expanded about 60-80% confluent first cell culture is about 75% confluent when the passaging at step c) occurs. In additional embodiments, the expanded about 60-80% confluent second cell culture is about 75% confluent when the passaging at step c) occurs.

In some embodiments, provided herein are methods of generating myoblast chimeric cells (MCCs) comprising: a) combining first and second populations of cultured myoblast cells to generate a cell mixture, wherein the first population of cultured myoblast cells comprises first cultured myoblast cells derived from a first subject a muscle disease (MD), and wherein the second population of cultured myoblast cells comprises second cultured myoblast cells derived from a second subject without the MD; and b) adding a cell-fusion solution to the cell mixture to generate a cell fusion reaction such that a population of myoblast chimeric cells (MCCs) is generated, wherein each of the MCCs comprises one of the first cultured myoblasts and one of the second cultured myoblasts, and wherein the cell-fusion solution comprises polyethylene glycol (PEG) at a concentration of 0.5-1.5 g/ml or 1.0-1.3 g/ml (e.g., 05 . . . 0.65 . . . 0.7 . . . 1.0 . . . 1.1 . . . 1.2 . . . or 1.5 g/ml).

In certain embodiments, the first and second populations of cultured myoblast cells have each been passaged five or less times (e.g., three or four times each; or three times each). In some embodiments, the first and second populations of cultured myoblast cells have each been passaged either three or four times. In certain embodiments, the methods further comprise: c) adding a stopping mixture to the cell mixture such that the cell fusion reaction stops generating MCCs, wherein the stopping mixture is added to the cell mixture after at least 4.0 minutes, but not later than 8.0 minutes, after the cell-fusion solution is added to the cell mixture. In certain embodiments, the stopping mixture comprises compete cell media and/or blood serum, and/or platelet lysate solution.

In certain embodiments, the methods further comprise, prior to step a) and/or prior to step b), testing the first population of cultured myoblast cells and the second population of cultured myoblast cells, and determining at least one of the following criteria is met for the first population and for the second population: i) less than 10% of the cultured myoblast cells express CD34, ii) less than 10% of the cultured myoblast cells express CD45, iii) greater than 45% or 50% or 60% of the myoblast cells express CD56, and iv) greater than 45% or 50% or 60% of the myoblast cells express CD90. In certain embodiments, the first and second populations meet three or all four of the criteria. In certain embodiments, the methods comprise determining at least one of the following criteria is met for the first population and for the second population: i) less than 5 or 10% of the cultured myoblast cells express CD34, ii) less than 5 or 10% of the cultured myoblast cells express CD45, iii) greater than 45% or 50% or 70% of the myoblast cells express CD56, and iv) greater than 45% or 50% or 70% of the myoblast cells express CD90. In certain embodiments, the first and second populations meet at least one of the following additional criteria: i) greater than 80% cell viability, ii) greater than 20% or 60% Desmin (DES) expression, and iii) greater than at least 10% Dystrophin expression compared to a cultured myoblast (e.g., 10% . . . 30% . . . 50%). In other embodiments, the methods further comprise testing the population of MCCs and determining at least one of the following criteria is met: i) less than 5 or 10% of the MCCs express CD34, ii) less than 5 or 10% of the MCCs express CD45, iii) greater than 40% or 60% or 70% of the MCCs express CD56, and iv) greater than 60% or 70% of the MCCs express CD90. In some embodiments, the population of MCCs meets three or all four of the criteria.

In some embodiments, the first and second populations of cultured myoblast cells have each been passaged five or less times. In other embodiments, the first and second populations of cultured myoblast cells have each been passaged three times. In further embodiments, the methods further comprise, prior to step a), labelling the first and second populations of cultured myoblast cells with different labels. In other embodiments, the different labels are different cell stains. In further embodiments, the methods further comprise: c) purifying the MCCs based on the different labels. In some embodiments, the muscle disease (MD) of the first subject is a muscular dystrophy. In other embodiments, the muscular dystrophy is Duchenne muscular dystrophy. In certain embodiments, the MCCs are cultured 1-5 times and tested to determine that less than 97% of the cultured MCCs contain a label.

In some embodiments, provided herein are compositions, kits, or systems comprising: a population of 1-3 or 2-5 times passaged myoblast chimeric cells (MCCs), wherein each of the MCCs comprises: i) a first cultured myoblast cell derived from a first human subject with a muscle disease (MD), and ii) a second cultured myoblast cell derived from a second human subject without the MD (e.g., a healthy donor). In further embodiments, the 1-3 or 2-5 times passaged MCCs meet at least one of the following criteria: i) less than 5 or 10% of the MCCs express CD34, ii) less than 5 or 10% of the MCCs express CD45, iii) greater than 50% or 60% or 70% of the MCCs express CD56, and iv) greater than 50% or 60% or 70% of the MCCs express CD90. In certain embodiments, the population of 1-3 or 2-5 times passaged MCCs meet three or all four of the criteria. In other embodiments, the population of 1-3 or 2-5 times passaged MCCs meets at least one of the following additional criteria: i) greater than 80% cell viability, ii) greater than 20% or 40% or 60% Desmin (DES) expression, and iii) greater than 10% compared to a cultured myoblast (e.g., 10% . . . 30% . . . 50%) expression.

In some embodiments, the population of 1-3 or 2-5 times passaged MCCs are the result of one passage. In other embodiments, the population of 1-3 or 2-5 times passaged MCCs are the result of two passages. In further embodiments, the population of 1-3 or 2-5 times passaged MCCs are the result of three passages. In certain embodiments, the myoblasts and/or MCC cells are seeded in culture in a range of 15-25%. In other embodiments, the myoblasts and/or MCCs are harvested in a range of 50-75%.

In certain embodiments, provided herein, are methods of treating a muscle disease comprising: administering the compositions of MCCs described herein to the first subject. In further embodiments, the muscle disease (MD) of the first subject is a muscular dystrophy. In additional embodiments, the muscular dystrophy is Duchenne muscular dystrophy.

In some embodiments, provided herein are kits or systems comprising: a) first and second populations of cultured myoblast cells, wherein the first population of cultured myoblast cells comprises first cultured myoblast cells derived from a first subject with a (MD), and wherein the second population of cultured myoblast cells comprises second cultured myoblast cells derived from a second subject without the MD; and b) reagents for detecting expression of at least one of the following on the cultured myoblast cells: CD34, CD45, CD56, and CD90. In certain embodiments, first and second populations of cultured myoblast cells have each been passaged three or less, or four or less times. In other embodiments, the first and second populations of cultured myoblast cells have each been passaged three times.

In some embodiments, provided herein are kits and systems comprising: a) a population of myoblast chimeric cells (MCCs), wherein each of the MCCs comprises: i) a first cultured myoblast cell from a first subject with muscle disease (MD), and ii) a second cultured myoblast cell from a second subject without the MD; and b) reagents for detecting expression of at least one of the following on the MCCs: CD34, CD45, CD56, and CD90. In further embodiments, the MCCs have been passaged 1-3 or 2-5 times or 6-7 times.

In certain embodiments, provided herein are kits and systems comprising: a) first and second populations of cultured myoblast cells, wherein the first population of cultured myoblast cells comprises first cultured myoblast cells derived from a first subject with a muscle disease (MD), and wherein the second population of cultured myoblast cells comprises second cultured myoblast cells derived from a second subject without the MD; and b) a cell-fusion solution comprising polyethylene glycol (PEG) at a concentration of 0.5-1.5 g/ml or 1.0-1.3 g/ml. In particular embodiments, the first and second populations of cultured myoblast cells have each been passaged four or less times. In other embodiments, the first and second populations of cultured myoblast cells have each been passaged three times.

In certain embodiments, the myoblasts and/or MCC cells are seeded in culture in a range of 15-25%. In other embodiments, the myoblasts and/or MCCs are harvested in a range of 50-75%.

In some embodiments, provided herein are methods of culturing and testing myoblast chimeric cells comprising: a) establishing a first cell culture of myoblast chimeric cells (MCCs) in a first container, wherein each of the MCCs comprises: i) a first cultured myoblast cell derived from a first subject with Duchenne muscular dystrophy (MD), and ii) a second cultured myoblast cell derived from a second subject without MD; b) culturing the first cell culture in the first container until an expanded about 60-80% confluent first cell culture is established that has at least twice as many MCCs as the first cell culture: c) sub-culturing at least a portion of the expanded about 60-80% confluent first cell culture into a second container such that a second cell culture is established in the second container; and d) culturing the second cell culture in the second container until an expanded about 60-80% confluent second cell culture is established that has at least twice as many MCCs as the second cell culture.

In particular embodiments, provided herein are methods of generating myoblast chimeric cells comprising: a) testing a first population of cultured myoblast cells and a second population of cultured myoblast cells and determining at least one of the following criteria is met for the first population and for the second population: i) less than 5 or 10% of the cultured myoblast cells express CD34, ii) less than 5 or 10% of the cultured myoblast cells express CD45, iii) greater than 45% or 50% or 60% or 70% of the myoblast cells express CD56, iv) greater than 45% or 50% or 60% or 70% of the myoblast cells express CD90, wherein the first population of cultured myoblast cells is derived from a first subject with a muscle disease (MD), and wherein the second population of cultured myoblast cells is derived from a second subject without the MD; and b) combining the first and second populations of cultured myoblast cells under cell fusion conditions such that a population of myoblast chimeric cells (MCCs) is generated, wherein each of the MCC's comprises a myoblast cell from the first subject and a myoblast cell from the second subject.

In certain embodiments, provided herein are methods of culturing and testing myoblast chimeric cells comprising: a) establishing: i) in a first MD container, a first MD cell culture of myoblast cells derived from a first subject with a muscle disease (MD), and ii) in a first Donor container, a first Donor cell culture of myoblast cells derived from a second subject without MD; b) culturing: i) the first MD cell culture in the first MD container until a MD expanded 60-80% confluent first cell culture is established that is adherent and has at least twice as many cells as the MD first cell culture; and ii) the first Donor cells culture in the first Donor container until a Donor expanded 60-80% confluent first cell culture is established that is adherent and has at least twice as many cells as the Donor first cell culture; c) passaging at least a portion of: i) the MD expanded 60-80% confluent first cell culture into a second MD container such that a second MD cell culture is established in the second MD container; and ii) the Donor expanded 60-80% confluent first cell culture into a second Donor container such that a second Donor cell culture is established in the second Donor container; d) culturing: i) the second MD cell culture in the second MD container until a MD expanded 60-80% confluent second cell culture is established that is adherent and has at least twice as many cells as the MD second cell culture; and ii) the second Donor cell culture in the second Donor container until a Donor expanded 60-80% confluent second cell culture is established that is adherent and has at least twice as many cells as the Donor second cell culture; e) passaging at least a portion of: i) the MD expanded 60-80% confluent second cell culture into a third MD container such that a third MD cell culture is established in the third MD container; and ii) the Donor expanded 60-80% confluent second cell culture into a third Donor container such that a third Donor cell culture is established in the third Donor container; f) culturing: i) the third MD cell culture in the third MD container until a MD expanded 60-80% confluent third cell culture is established that is adherent and has at least twice as many cells as the MD third cell culture; and ii) the third Donor cell culture in the third Donor container until a Donor expanded 60-80% confluent third cell culture is established that is adherent and has at least twice as many cells as the Donor third cell culture; g) passaging at least a portion of: i) the MD expanded 60-80% confluent third cell culture into a fourth MD container such that a fourth MD cell culture is established in the fourth MD container; and ii) the Donor expanded 60-80% confluent third cell culture into a fourth Donor container such that a fourth Donor cell culture is established in the fourth Donor container; h) combining at least a portion of the fourth MD cell culture and the fourth Donor cell culture to generate a cell mixture, wherein neither has been passaged more than four times, and i) adding a cell-fusion solution to the cell mixture to generate a cell fusion reaction such that a population of myoblast chimeric cells (MCCs) is generated, wherein each of the MCCs comprises one of the first cultured myoblasts and one of the second cultured myoblasts.

In some embodiments, provided herein are composition comprising: a population passaged myoblast chimeric cells (MCCs), wherein each of said MCCs comprises: i) a first cultured myoblast cell derived from a first human subject with a muscle (MD), and ii) a second cultured myoblast cell derived from a second human subject without said MD; wherein said population of passaged MCCs has been passaged 1, 2, 3, 4, or 5 (or more) times; and wherein less than 97% of said population of passaged MCCs contain an exogenous dye. In certain embodiments, the less than 99% of said population of passaged MCCs contain an exogenous dye.

DESCRIPTION OF THE DRAWINGS

In FIG. 1, "MB" stands for Myoblasts. "DYS" stands for dystrophin expression and "DES" stands for desmin expression.

FIG. 3D indicates that there is no change of CD56 expression after fusion. FIG. 3E shows the average CD56 expression before staining with either PKH26 (pink) or PKH67 (green). The average of CD56 expression in myoblasts before staining with PKH (dark blue) is almost identical to the average CD56 expression in cells right after Fusion (blue). These figure show the importance of using myoblasts with the highest CD56 expression possible to ensure high CD56 expression level in cells after fusion.

FIG. 8 shows characterization of myoblasts (MB) cultured in media supplemented with 10% human platelet lysate: days between passages, population doubling time, viability and CD markers. FIG. 8A shows myoblasts, in general, should be cultured for about 10 days from the day of isolation from muscle biopsy to the passage p0→p1. About 3-5 days of culture in general is often needed between each of the subsequent passages p1→p2, p2→p3, p3→p4, p4→p5 and p5→p6. As in most cases the myoblast yield is sufficient for the Fusion at passage p2→p3. As a result, in general, the average duration of myoalsts culture before the Fusion is about 18 days. FIG. 8B shows the population doubling time of myoblasts culture is about 28 h between passage p1 to p2, and p2 to p3, and increases over time to about 33 h on passage p3 to p4. FIG. 8C shows the average cell viability of myoblasts measured with every passage fits in the range 80-100%. FIG. 8D shows the percentage of CD34 and CD45 positive cells in myoblasts culture is lower than 10%, while over 70% of cells express CD56 and CD90, as assessed on passages p1→p2, p2→p3, p3→p4, p4→p5 and p5→p6.

FIG. 9 shows characterization of Myoblast Chimeric Cells (MCC) cultured in media supplemented with 10% human platelet lysate, days between passages, population doubling time, viability and CD markers. FIG. 9A shows that, in general, MCC cells should be cultured for about 7 days from the day of Fusion and sorting to the passage p0→p1. About 5-7 days of culture is generally needed between each of the subsequent passages p1→p2, p2→p3, p3→p4, p4→p5 and p5→p6. The MCC yield is generally sufficient for the preparation of the Final product at passage p3→p4 or p4→p5. This means that, in general, the average duration of MCC culture lasts about 22-27 days. FIG. 9B shows that the population doubling time of MCC culture is about 131 h between sorting and passage p0 to p1, and about 37-60 h on subsequent passages and increases over time. FIG. 9C shows that the average cell viability of MCC measured with every passage fits in the range 80-100%. FIG. 9D shows that the percentage of CD34 and CD45 positive cells in myoblasts culture is lower than 10%, while over 50% of cells express CD56 and CD90, as assessed on passages p1→p2, p2→p3, p3→p4, p4→p5 and p5→p6.

DEFINITIONS

Figure 1A:
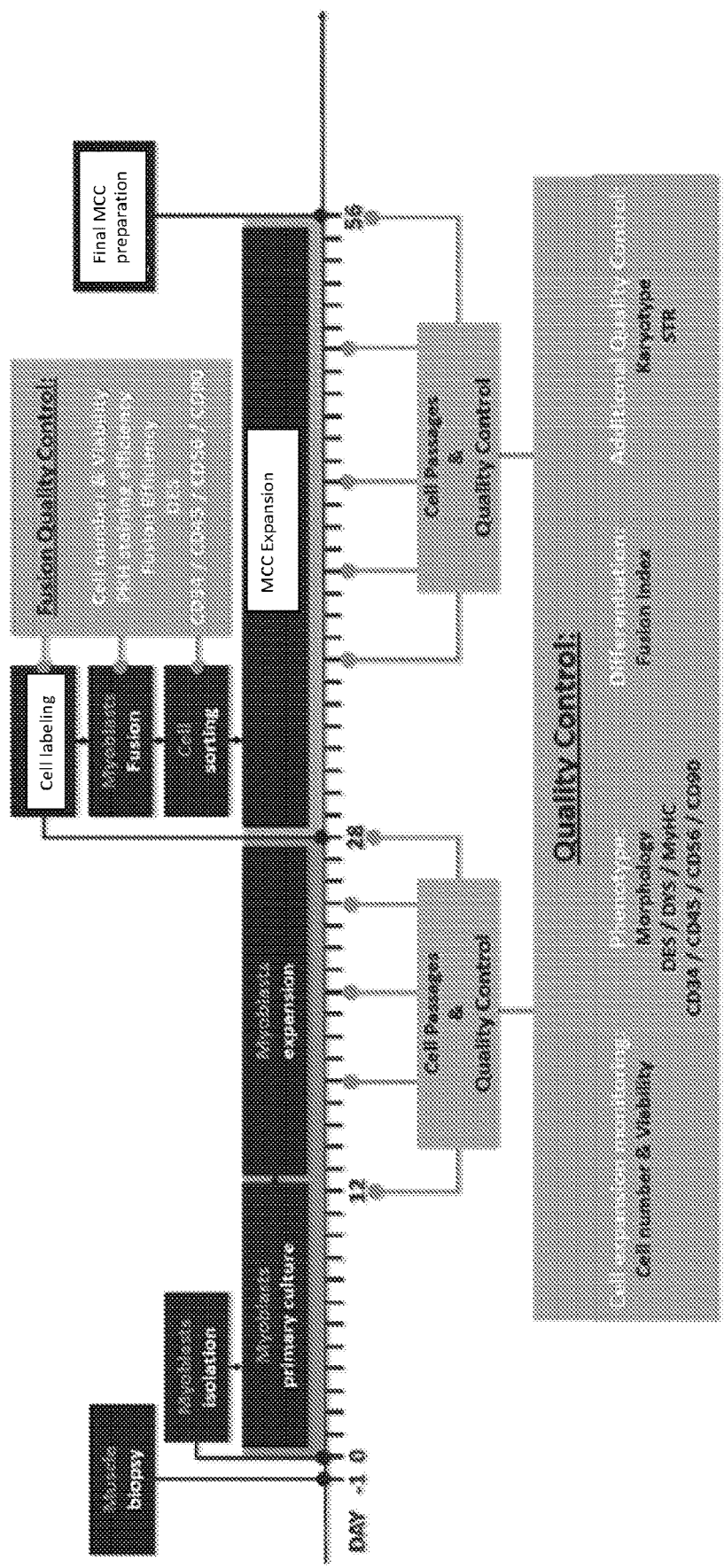
FIG. 1A shows an exemplary timeline for production of myoblast chimeric cells (MCCs), including: 1) muscle biopsy; 2) myoblast isolation; 3) myoblast primary culture; 4) myoblast expansion; 5) cell labeling; 6) myoblast fusion; 7) MCC cell sorting; 8) MCC expansion, 9) Final MCC preparation, 10) MCC Cells Qualification and Product Preparation, 11) Dosage and Administration to Treat Subject with MD, 12) Cryopreservation 13) Cell Banking, and 14) Exemplary Reagents. Also included are various quality control steps to test the cells as they move through the process e.g., assessment of the karyotype, CD markers, desmin, dystrophin, microbiology and endotoxins.
Figure 1B:
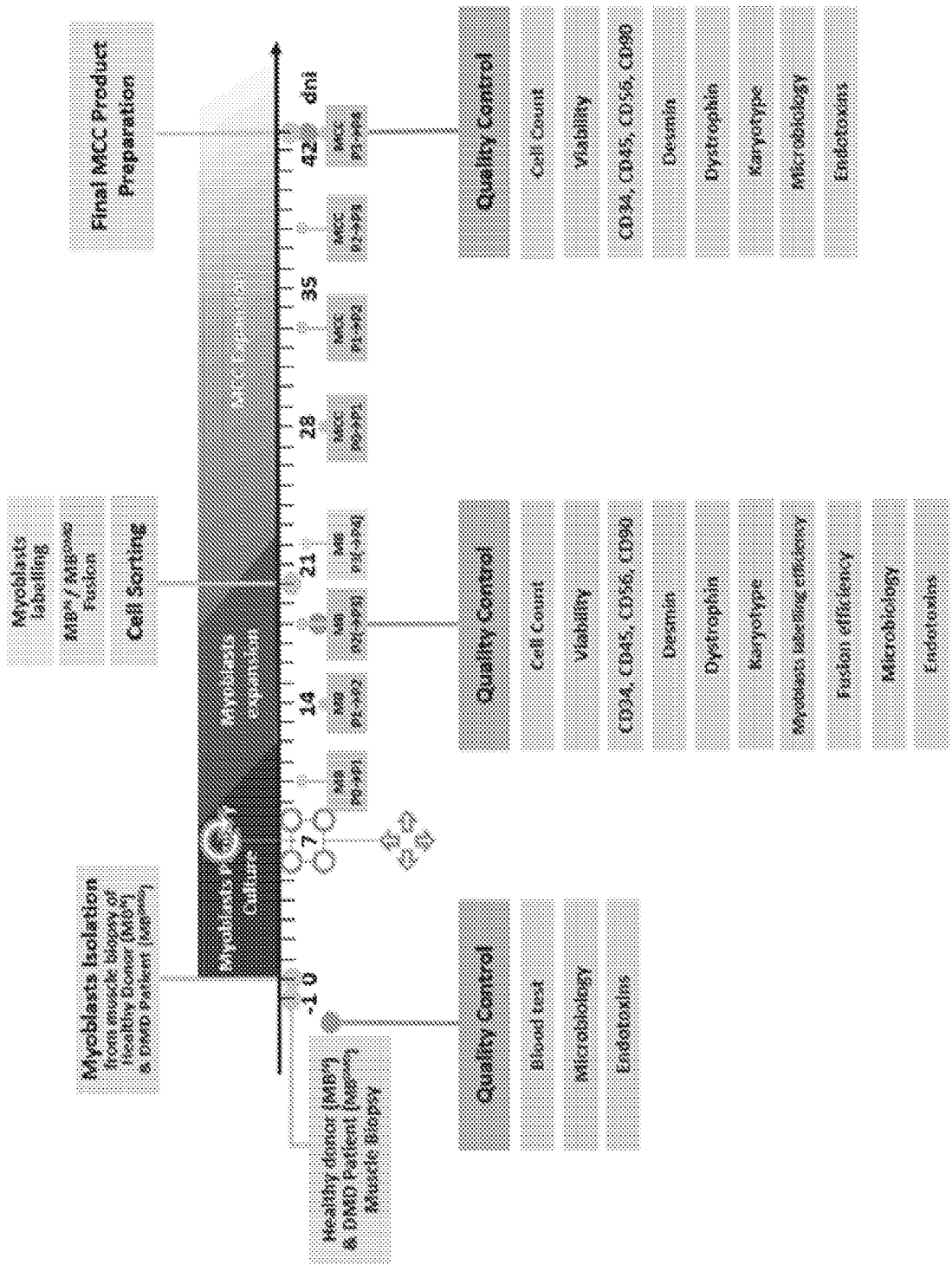
FIG. 1B shows an additional exemplary timeline for production for myoblast chimeric cells (MCCs).

As used herein, the terms "host," "subject" and "patient" refer to any animal, including but not limited to, human and non-human animals (e.g., dogs, cats, cows, horses, sheep, poultry, fish, crustaceans, etc.) that is studied, analyzed, tested, diagnosed or treated. As used herein, the terms "host," "subject" and "patient" are used interchangeably, unless indicated otherwise.

As used herein, "muscle disease" include, but are not limited to, any disease that involves disease states of the muscle tissue (e.g., of a human), such as a muscular dystrophy, a Myopathy, a Motor neuron diseases, an Ion channel disease, a Mitochondrial disease, a Neuromuscular junction disease, Peripheral nerve disease, and anti-aging muscle frailty-sarcopenia. Specific muscle diseases include, but are not limited to, Becker muscular dystrophy (BMD), Congenital muscular dystrophies (CMD) (e.g., Bethlem CMD, Fukuyama CMD, Muscle-eye-brain diseases (MEBs), Rigid spine syndromes, Ullrich CMD, and Walker-Warburg syndromes (WWS)), Duchenne muscular dystrophy (MD), Emery-Dreifuss muscular dystrophy (EMD), Facioscapulohumeral muscular dystrophy (FSHD), Limb-girdle muscular dystrophies (LGMD), Myotonic dystrophy (DM), Oculopharyngeal muscular dystrophy (OPMD), Congenital myopathies, Cap myopathies Centronuclear myopathies, Congenital myopathies with fiber type disproportion, Core myopathies, Central core disease, Multiminicore myopathies, Myosin storage myopathies, Myotubular myopathy, Nemaline myopathies, Distal myopathies, GNE myopathy/Nonaka myopathy/hereditary inclusion-body myopathy (HIBM), Laing distal myopathy, Markesberg-Griggs late-onset distal myopathy, Miyoshi myopathy, Udd myopathy/tibial muscular dystrophy, Vocal cord and pharyngeal distal myopathy, Welander distal myopathy, Endocrine myopathies, Hyperthyroid myopathy, Hypothyroid myopathy, Inflammatory myopathies, Dermatomyositis, Inclusion-body myositis, Polymyositis, Metabolic myopathies, Acid maltase deficiency (AMD, Pompe disease), Carnitine deficiency, Carnitine palmityl transferase deficiency, Debrancher enzyme deficiency (Cori disease, Forbes disease), Lactate dehydrogenase deficiency, Myoadenylate deaminase deficiency, Phosphofructokinase deficiency (Tarui disease), Phosphoglycerate kinase deficiency, Phosphoglycerate mutase deficiency, Phosphorylase deficiency (McArdle disease), Myofibrillar myopathies (MFM), Scapuloperoneal myopathy, ALS (amyotrophic lateral sclerosis), Spinal-bulbar muscular atrophy (SBMA), Spinal muscular atrophy (SMA), Andersen-Tawil syndrome, Hyperkalemic periodic paralysis, Hypokalemic periodic paralysis, Myotonia congenita, Becker myotonia, Thomsen myotonia, Paramyotonia congenita, Potassium-aggravated myotonia, Friedreich's ataxia (FA), Mitochondrial myopathies, Kearns-Sayre syndrome (KSS), Leigh syndrome (subacute necrotizing encephalomyopathy), Mitochondrial DNA depletion syndromes, Mitochondrial encephalomyopathy, lactic acidosis and stroke-like episodes (MELAS), Mitochondrial neurogastrointestinal encephalomyopathy (MNGIE), Myoclonus epilepsy with ragged red fibers (MERRF), Neuropathy, ataxia and retinitis pigmentosa (NARP), Pearson syndrome, Progressive external opthalmoplegia (PEO), Congenital myasthenic syndromes (CMS), Lambert-Eaton myasthenic syndrome (LEMS), Myasthenia gravis (MG), Charcot-Marie-Tooth disease (CMT), and Giant axonal neuropathy (GAN).

DETAILED DESCRIPTION OF THE INVENTION

The present invention relates to methods and compositions for generating and using myoblast chimeric cells (MCCs) for treating a muscle disease, such as muscular dystrophy, where the MCCs are composed of a myoblast derived from a patient with muscle disease (MD) and a myoblast from a donor without the MD (e.g., a healthy donor). In certain embodiments, cell fusion methods are performed using 2-4 or 5 times passaged myoblasts from the MD and donor subject, and/or polyethylene glycol at 0.5-1.5 g/ml or 1.0-1.3 g/ml. In other embodiments, the MCCs created by fusion are passaged 1-4 or 5 times before use, and are passaged at 60-80% confluency. In further embodiments, the myoblasts and/or MCCs are tested at any stage during the process for less than 5-10% CD34 and/or CD45 expression, and/or greater than 45% or 60-70% CD56 and/or CD90 expression.

1. Muscle Biopsy from MD Patient and Myoblast Donor

Muscle tissue is collected from both a patient with DMB and a myoblast donor (e.g., relative of the patient with DMB, or an un-related person) as source of myoblasts. Such tissue is generally collected by a muscle biopsy. Methods of such muscle tissue collection (e.g., skeletal muscle tissue) are known in the art (e.g., Spinazzola et al; Bio Protoc. 2017 November 5; 7(21): e2591, herein incorporated by reference). Due to the possible different amount of time needed for the expansion of myoblasts isolated from the healthy donor and DMB patient, it may be necessary to perform the biopsies at different time points. An exemplary protocol for such muscle biopsy is as follows below.

Exemplary Tissue Collection Procedure:

Before starting the tissue collection procedure, the serology status (e.g., HBV (anti-HBc, HBsAg), HCV (anti-HCV), HIV (anti-HIV1/2), HTLV I/II (anti-HTLV I/II), Epstein-Barr Virus (EBV), cytomegalovirus (CMV) and Syphilis (VDRL, TPHA and/or FTA)) of the patient should be checked. In general, if any of the serology results are positive, particularly for the donor, it may be best to find a different donor.

On the day the skeletal muscle tissue collection is performed, 2 EDTA tubes of 4.5 ml each are collected for a serology status and nucleic acid testing (e.g., PCR HIV, PCR HBV and PCR HCV) to be performed at a testing laboratory. Skeletal muscle tissue collection is generally performed on the lateral portion of the over the palpated vastus lateralis or biceps or deltoid muscle of the upper arm based on the assessment of muscle function. The biopsy will result in harvesting 1 cm3 of tissue volume. The biopsy site where muscle tissue is collected should be free from previous injuries, contractures or instrumentation. The patient may be administered an opioid analgesics (ex. 50 mg Tradonal Odis®) 20 to 30 minutes before sampling. Blood is also collected from the patient at the same time (e.g., collect blood in 2 EDTA tubes; at least 4.5 ml in each tube). Collected tissue samples are kept at a temperature between +2 and +8° C. and shipped if necessary at 4 degrees Celsius in transport medium. Blood samples are shipped, if necessary, at room temperature.

In case of the MD patient, skeletal muscle tissue collection is performed in the operating room under general anesthesia. A biopsy from a healthy donor (e.g., allogenic) of skeletal muscle tissue is performed under local anesthesia. The MD and healthy subject will undergo standard intratracheal general inhaled anesthesia type TIVA (Total IntraVentive Anesthesia) with the use of profopol and remifentanil (Ultiva®, GSK). The subjects will not receive any inhalation anesthetics or "depolarizing" muscle relaxants. If necessary, non-depolarizing short-acting relaxants are used in small doses.

A harvesting technique of skeletal muscle (open biopsy) is as follows. Based on the assessment of muscle function, muscle tissue biopsy will be taken from: 1) the lateral portion of the thigh over the palpated vastus lateralis or 2) from the biceps or 3) deltoid muscle of the upper arm. Sterile technique should be applied at all times during the procedure. The following procedures are used. 1) A suitable pre-medication of benzodiazepine and oral analgesia is given if required and the patient is positioned on the operating table. The skin is prepared and draped in a standard sterile fashion. Timely infiltration with generous quantities of quick-acting local anesthetic to the skin and subcutaneous tissues, but not the muscle is performed. Pain on local anesthetic infiltration can be reduced by using smaller gauge needles, using dilute and warm (37 degree C.) solutions, and by injecting slowly. Due to the risk of producing artefacts in the biopsy specimen, adrenalin and infiltration into the muscle with local anesthetic should not be used. 2) A 5-cm longitudinal incision is performed followed by sharp atraumatic dissection to the fascia without the use of diathermy. Ideally, the incision should be orientated with regard to Langer's lines to optimize cosmesis while allowing a wide exposure of longitudinal muscle fibres. If the vastus lateralis is chosen, a more lateral approach is generally ideal to minimize dissection through the adipose tissue and avoid arterial perforators. If the biceps or deltoid muscle is chosen, the approach is similar and includes a 5-cm longitudinal skin incision, followed by tissue dissection down to the fascia and muscle belly exposure. 3) One biopsy of 1-2 cm by 0.5-0.8 cm are sharply excised from the muscle belly away from the myofascial regions in order to harvest muscle sample of approx. 1 cm3 of volume. 4) Place the harvested muscle in sterile container. 5) Prior to closure, absolute haemostasis should be ensured and the wound sutured in layers taking care to close the fascia to prevent post-operative muscle herniation. Interrupted nylon sutures to the skin provide strength, although usually a sub-cuticular absorbable suture is sufficient. 6) Apply a suitable dressing followed by a compressive bandage at the surgeon's discretion. 7) Post-operatively the patient is encouraged to elevate the limb, mobilize as tolerated but to avoid strenuous activity or exercise until the wound has healed.

A needle biopsy technique is as follows. 1) The skin is prepared and draped in a standard sterile fashion. Timely infiltration with generous quantities of quick-acting local anesthetics to the skin and subcutaneous tissues, but not the muscle is performed. Pain on local anesthetics infiltration can be reduced by using smaller gauge needles, using dilute and warm (37 degree C.) solutions, and by injecting slowly. Due to the risk of producing artefacts in the biopsy specimen, adrenalin and infiltration into the muscle with local anesthetics must not be used. 2) The small stab incision is made with #11 surgical blade down to the fascia. 3) The muscle biopsy needle is introduced perpendicularly into the incision. 4) The biopsy needle is pushed through the fascia to the muscle belly for muscle biopsy harvest. A semi-automatic biopsy needle for soft tissues with a detachable cannula may be used to perform a needle biopsy (Manufacturer: MEDAX Medical Devices, 14 G, 16 cm, Model: 14GX160MM, ref number: REF LX14160-00). 5) Place the harvested muscle in sterile container. 6) Apply pressure for several minutes to the incision site for haemostasis. 7) Apply a suitable dressing followed by a compressive bandage at the surgeon's discretion.

Labelling and packaging of the skeletal muscle sample may be performed as follows. Using a sterile pen: 1) enter the patient ID and date of skeletal muscle tissue collection on a container with skeletal muscle tissue biopsy (primary pack). Write the patient ID and date of skeletal muscle tissue biopsy on two labels, then place one sticker on each of the two transparent plastic bags used as the secondary and tertiary container of the primary container. 2) Write down the patient ID and the date and time of blood collection on labels for two EDTA tubes. Place both test tubes in one unlabeled, transparent plastic bag. In certain embodiments, the containers (e.g., tubes) with muscle tissue should be shipped in 2° C.-8° C. temperature range in appropriate temperature controlled packaging.

2. Myoblast Isolation from Muscle Biopsy

Next, myoblasts are isolated from muscle tissue is collected from both a patient with DMB and a myoblast donor (e.g., relative of the patient with DMB, or an un-related person). Methods of such myoblast isolation are known in the art (e.g., Spinazzola et al; Bio Protoc. 2017 Nov. 5; 7(21): e2591, herein incorporated by reference). An exemplary protocol for such muscle biopsy is as follows below.

Exemplary Isolation of Myoblasts from Tissue

This exemplary procedure describes the course of myoblast isolation from muscle tissue. Equipment, reagents, and materials to be used: Equipment, reagents, materials and accessories:

Equipment: Falcon tubes, 50 ml; Petri dish, sterile; Scalpels×2; Syringe, 20 ml; 0.02 μm syringe filter; Cell Strainers, 70 μm, 2 pcs; Serological pipettes, 2 ml; and T25 flask.

Reagents: HBSS (Hank's Balanced Salt Solution); Cell culture medium; Collagenase; and Gelatin 1% (in H20) or MSC Attachment 1% solution (Biological Industries)

Accessories: Medical gloves; Disinfectant liquid; and Disposable, lockable container.

An exemplary protocol for isolation of myoblasts from muscle biopsy should is as follows. First, coat the bottom of the T25 flask with 1% gelatin by adding about 1 ml of gelatin to the T25 bottle. Make sure the gelatin evenly covers the growth area ow the flask. Gently tap the flask if needed. Incubate the T25 flask with gelatin for 5 minutes in the thermostat, until gelatin has set. After this time, take the T25 out of the thermostat and remove excess of gelatin with sterile serological pipette if needed. Next, adjust the thermomixer thermoblock to 33 degrees C. Next, measure off 0.04 g of collagenase into the 50 ml Falcon tube using a digital scale. Transfer the Falcon tube with collagenase into the laminar chamber. Dissolve the collagenase in 20 ml HBSS medium using serological pipette and pipetting several times. Filter the dissolved collagenase into a new Falcon tube using a syringe and 0.02 μm syringe filter. Next, place the muscle biopsy in a Petri dish and use the scalpel to remove the (yellow) fat and (white) connective tissue. Cut the tissue with two scalpels until it is minced to the pulp consistency. Next, transfer the minced tissue to a Falcon tube with collagenase. Mix well, recap the tube and secure it with parafilm. Next, place the parafilm-sealed tube in thermoblock (33° C.) with intensive shaking. Incubate 45 min. Mix well every 15 minutes and monitor the progress of digestion. Next, filter the digested tissue using a 70 μm cell strainer and a Pasteur pipette into a new Falcon tube. Rinse the strainer with HBSS. Next, add HBSS to a volume of 50 ml to inactivate collagenase. Next, centrifuge at 1200 rpm, 10 min, RT. Finally, gently remove the supernatant using a serological pipette. Be careful not to disturb the pellet as it might be loose.

3. Myoblast Primary Culture

Figure 2:
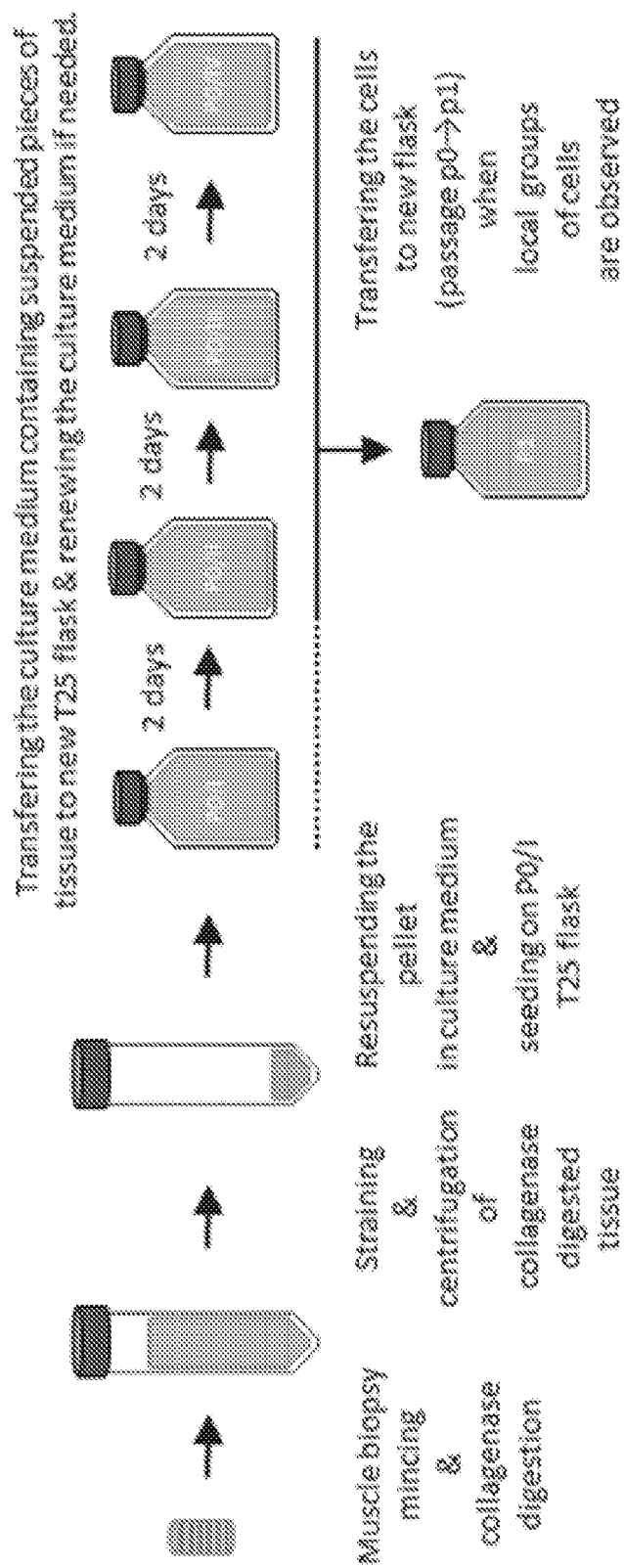
FIG. 2 shows an exemplary schematic for moving from muscle tissue biopsy to expanded myoblast cell line cultures.

Myoblast primary culture procedures are known in the art. FIG. 2 provides a general schematic for such a procedure. An exemplary protocol is as follows. First, the resuspend the pellet (e.g., see above) in 5 ml of cell culture medium and transfer the suspension into a gelatin-coated or Attachment-coated T25 flask using a serological pipette. Sign the T25 flask as passage 0/I. Then, every two days, transfer the contents of the flask into the new T25 flask, until pouring into the fourth T25 flask. Each time sign the new bottle as passage 0 and add number of the bottle. With each transfer, add 2 ml of fresh medium to the transferred suspension and 5 ml of fresh medium to the empty bottle. Change the media every 2-3 days and passage the cells as soon as groups of cells are visible under the microscope in order to avoid spontaneous differentiation. This will be the first passage, and is denoted P1.

4. Myoblasts Expansion

Figure 3:
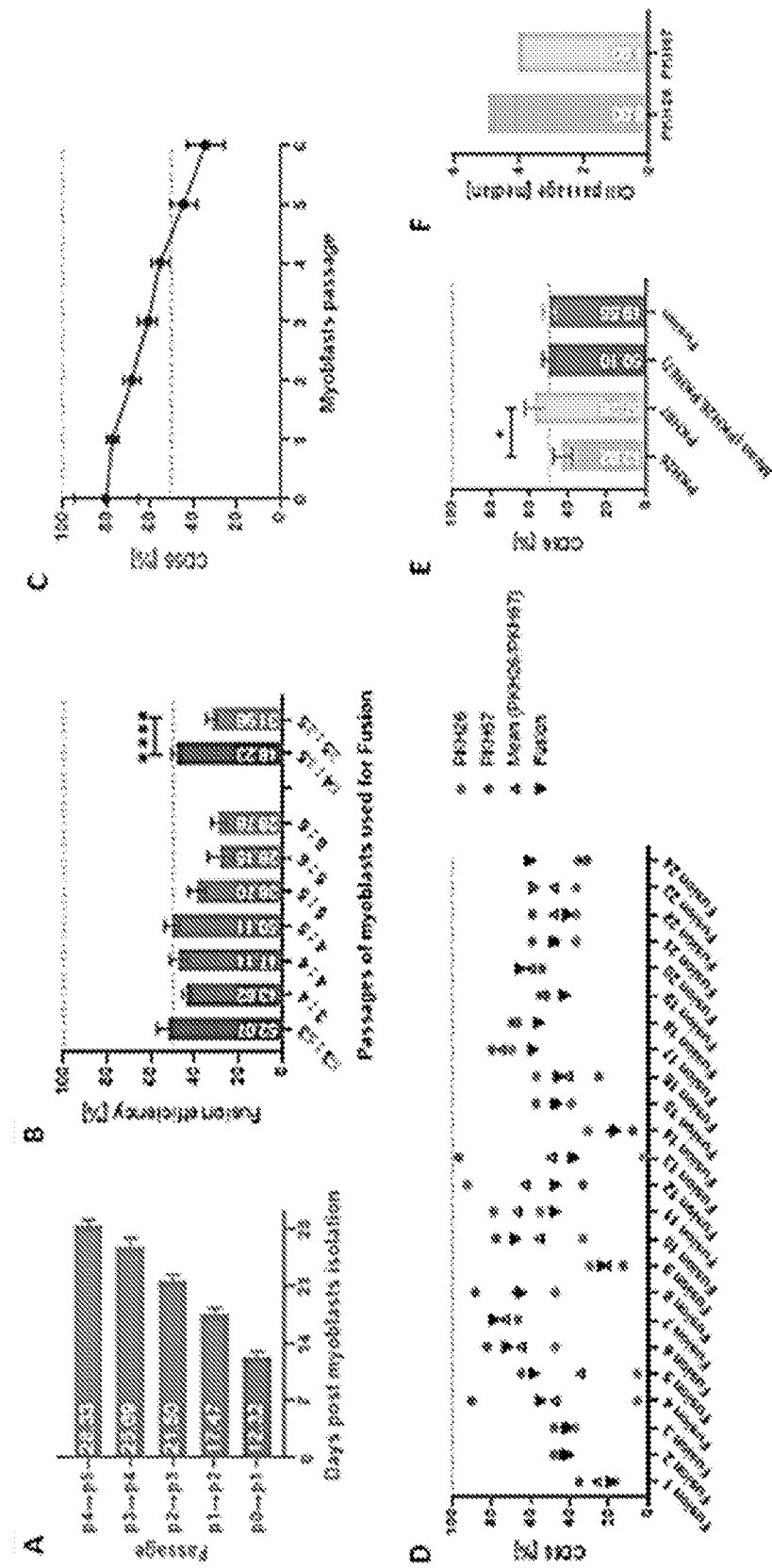
FIG. 3A shows the average number of days from myoblasts isolation to each myoblast passage. The fusion efficiency starts to decrease when both myoblasts cell lines are on passage 5 or higher.
FIG. 3B shows fusion efficiency of various combinations of passaged parental cells, where the combination of 3:3 (both cell lines passaged 3 times) had the highest efficiency.
FIG. 3C shows results showing that CD56 expression in myoblasts decreases over time and passages.
FIG. 3D shows the CD56 expression for myoblasts line before staining with either PHK26 (red dots) or PKH67 (green dots) as well as the expression of CD56 in myoblasts after Fusion (black triangles) and the mean CD56 expression in myoblasts stained with PKH26 and myoblasts stained with PKH67 (clear triangles).
FIG. 3E sums up the results shown in Figure DD.
FIG. 3F shows the difference of CD56 expression in myoblasts subject to the PKH26 and PKH67 staining is the result of the difference in the average passage number, not the result of staining with particular PKH dye.

Next, the cultured myoblast cells may be expanded by multiple rounds of passage and expansion. As described in FIG. 3, it is beneficial to have both the MD and donor cell lines be at passage five or earlier, or not later than four (e.g., both donor and DMC cell lines are at passage 3) when subjected to the fusion protocol, although in some cases cells at passage five may be u as long as they meet the quality control criteria (e.g., less than 10% CD34 and/or CD45 expression, and/or greater than 40% CD56 and/or CD90 expression) An exemplary myoblast expansion protocol is as follows.

First, expand the MD and donor cultured myoblast cells between 60-80% confluency into flasks up to Passage six, but preferably only up to Passage three or four. In certain embodiments, the donor and MD cultured myoblasts are passaged a total of three times since the primary culture phase. The lower the passage number the more normal the cell as you are avoiding mutations, differentiation, senescence, and more. Passage and expansion may be achieved as follows. Pour the media out of the flask under a hood for sterility. Rinse flask with sterile 1×PBS by adding and distributing the PBS within the flask and pouring it out (add 5-7 mL for a T-75 flask; add 10 mL for a T-182 flask; and add 25 mL for a T-1000 flask). Add 0.25% Trypsin or TrypLE solution (or other disassociating agent) to flask for 5-7 minutes to completely dissociate the cells from the surface of the flask (add 3 mL for a T-75 flask; add 5 mL for a T-182 flask; and add 25 mL for a T-1000 flask). Ensure all cells have dissociated via observation under the microscope. Next, add 2× the amount of disassociating agent added of any complete media (DMEM/RPMI/MEM+10% or 10-20% FBS or human Platelet Lysate Solution +1% Antibiotic) to inactivate the trypsin.

Aspirate or pour cells into 50 mL conical tube. Rinse flask 1-2× more with sterile 1× PBS to assure all cells have been collected. Observe flask under a microscope for cells. Centrifuge all conical tubes at 1300-1500 rpm for 5 minutes. Consolidate cells into one 50 mL conical tube. Resuspend cells with 10 mL of sterile 1×PBS or sterile DMEM+AA or complete cell culture medium (depending on size of pellet) and take a sample for counting and assessing viability and a sample for unstained controls. Add at least 100 uL sorting buffer to unstained controls to dilute the cells. Unstained control should be pipetted into test tube. Count cells using hemocytometer or automatic cell counter. Cells are now prepared for either seeding into new flasks or continuing on to staining and fusing.

5. Myoblasts Qualification

Prior and/or after the procedures below (e.g., staining, fusion, cell sorting, and prior to MCC expansion), both the donor and MD myoblast cell lines are tested to ensure certain criteria are met. In certain embodiments, the cells are examined to determine that there are 4-20 million cells in each cell line (e.g., 4 . . . 6 . . . 12 . . . 20 million). In other embodiments, the cells are examined to ensure at least 80% viability (e.g., at least 80% . . . 85% . . . or 90% viability). In certain embodiments, the cells are tested to ensure that they have less than 10% (e.g., less than 10 . . . 7 . . . or 5%) of CD34 and/or CD45 expression. In some embodiments, the cells are tested to ensure that they have at least 50% or 60% (e.g., 50% . . . 60% . . . 65% . . . 70%) of CD56 and/or CD90 expression. In particular embodiments, the cells are tested to ensure they have at least 40% or 60% (e.g., 50% . . . 60% . . . 65% . . . 70%) desmin (DES) protein expression and/or at least 10% dystrophin expression. In certain embodiments, some or all of these above testing is performed before and after the staining, fusion, cell sorting, and prior to MCC expansion described further below.

Exemplary Marker Detection Protocols

The following exemplary protocols can be used to detect the cell surface markers using antibodies. These exemplary procedures describe the labeling of CD34, CD45, CD56 and CD90 markers with antibodies conjugated to fluorochromes. The various cell samples for the procedure should be collected under the laminar chamber, but the rest of the procedure is performed outside the laminar chamber, on the laboratory bench. Determination of CD markers expression on samples taken from the cell culture should be carried out during each passage of cells. However, in general, when the cell count is too low (on the passage p0→p1 of primary myoblasts culture) it can be omitted, but should be carried out during the next earliest passage possible.

The following equipment, reagents, materials and accessories are used. Equipment: i. 96-well plate, V-shaped, non-sterile. ii. Automatic pipette with a range of 2-200 μl. iii. Pipette tips with a range of 2-200 μl. iv. Automatic pipette with a range of 0.1-10 μl. v. Pipette tips with a range of 0.1-10 μl. and vi. Cytometric tubes. Reagents: i. A suspension of cells prepared for passage. ii. 10% Formalin, buffered (4% PFA). iii. 1% FBS solution (in PBS). iv. Antibodies: 1. APC anti-human CD34 Antibody (BioLegend, 343510), 2. PE/Cy7 anti-human CD45, Antibody (BioLegend, 304016), 3. APC Mouse Anti-Human CD56 Clone B159 (BD Pharmingen™, 555518). and 4. PE/Cy7 anti-human CD90 (Thy 1) Antibody (BioLegend, 328124). Accessories: i. Medical gloves, ii. Disinfectant liquid, iii. Disposable, lockable container.

The procedure of CD markers labeling should be proceeded as follows. First, sign the lid of the 96-well plate with the ID of the cell line and its passage. Mark three wells to which NS (no stain), CD34/45 (CD34+CD45) and CD56/90 (CD56+CD90) stained samples will be applied.

If samples from more than 1 cell line would be labeled, mark more wells, accordingly. Next, sign three cytometric tubes with the cell line ID, passage, date of sample collection and labelling, and the "NS", "CD34/45" or "CD56/90", respectively. For more than one cell line, prepare more tubes accordingly. Next, transfer 100-300 k cells to each one of the three prepared wells (NS, CD34/45, CD56/90) of 96-well plate. The maximum capacity of the 96-well dish is 3000 Next, centrifuge the 96-well plate with samples, 1400 rpm, 5 min. Next, remove the supernatant by quickly turning the 96-well plate upside down over the disposable, lockable container. Next, using the automatic pipette resuspend the cell pellets in each well in 200 μl 1% FBS. Next, centrifuge the 96-well plate with samples, 1400 rpm, 5 min. While the plate is being centrifuged prepare the dilutions of antibodies as follows: Label per 1 well of 96-well plate*: i) NS (No Stain) 50 μl 1% FBS; ii) CD34/4550 μl 1% FBS; iii) +0.25 μl APC anti-human CD34 Antibody; iv) +0.25 μl PE/Cy7 anti-human CD45 Antibody; v) CD56/90 50 μl 1% FBS; vi) +2 μl APC Mouse Anti-Human CD56 Clone B159; and vi) +1 μl PE/Cy7 anti-human CD90 (Thy 1) Antibody. *In the case of labelling the CD of more than 1 cell line, the amount of prepared dilutions of antibodies should be increased proportionally, bearing in mind the surplus of reagents corresponding to the amount for 1 well (or 10%).

Next, remove the supernatant from the centrifuged plate by quickly turning the plate upside down over the disposable, lockable container. Next, resuspend the cell pellets in each well in the previously prepared dilution of antibody, according to the labels on the 96-well lid. Next, incubate the plate with cells and added antibodies for 20 minutes in the dark. Next, after the incubation, add 100 μl of 1% FBS to each well. Next, centrifuge the 96-well plate, 1400 rpm, 5 minutes. Next, remove the supernatant from the centrifuged plate by quickly turning the plate upside down over the disposable, lockable container. Next, resuspend the cell pellets in each well in 200 μl of 1% FBS. Next, centrifuge the 96-well plate, 1400 rpm, 5 minutes. Next, remove the supernatant from the centrifuged plate by quickly turning the plate upside down over the disposable, lockable container. Next, for the cell fixation, resuspend the cell pellets in each well in 200 μl of 1% PFA, and transfer the contents of each well to appropriately signed cytometric tubes. Finally, cytometric analysis after CD labeling should be carried out as soon as possible.

If it is not possible to analyze the samples on the same day, labeled and fixed cells can be stored in a refrigerator (e.g., 2° C.-8° C.) in the dark, in covered test tubes (to prevent evaporation) and analyzed in a flow cytometer within 2-3 days.

The following protocols can be used for assessment of desmin expression, dystrophin expression, and myosin heavy chains (MyHC) expression, using antibody detection. The Immunocytofluorescence labeling is performed on cells cultured on coverslips that has been placed in the wells of a 12-well dish. Desmin: cells that adhered to the coverslips and have been cultured in growth medium for 1-2 days. Dystrophin: cells that adhered to the coverslips, have grown to 80-90% confluency in the growth medium and have been cultured in the differentiation medium for 7 days. MyHC: cells that adhered to the coverslips, have grown to 80-90% confluency in the growth medium and have been cultured in the differentiation medium for 7 days.

Equipment: a. 12-well plates with cover slips on which cells has been cultured; b. Pasteur pipettes; c. Petri dish, ø15 cm; d. Paper towel; e. Parafilm. Reagents: a. PBS, without Ca/Mg ions, b. 10% Formalin, buffered (4% PFA), c. 0.1% Triton x-100 in PBS, and d.

Blocking Buffer:

PBS (94.5%) with and addition Human albumin (CSL Behring 200 g/l) (5%) and Triton X-100 (Sigma T8787-50 ML) (0.5%). Antibodies: Monoclonal Anti-Dystrophin antibody produced in mouse, clone MANDYS8 (Sigma-Aldrich, D8168-0.2 ML); Monoclonal Anti-Desmin antibody produced in mouse, clone DE-U-10 (Sigma-Aldrich, D1033-0.2 ML); Monoclonal Anti-Myosin (Skeletal, Slow) antibody produced in mouse, clone NOQ7.5.4D (M8421-0.2 ML); Secondary antibody goat anti-mouse (FITC) (NOVUSBIO, NB7510) Fluoroshield with DAPI (Sigma-Aldrich, F6057-20 ML)

The procedure should be proceeded as follows. Cell fixation and permeabilization: i. Rinse the coverslips with cells in PBS; ii. Fix cells by adding buffered formalin (4% PFA in PBS), 15 minutes, 4° C.; iii. Rinse 3×5 minutes in PBS; iv. Permeabilize cells for 15 minutes at room temperature with 0.1% Triton X-100 in PBS; v. Rinse 3×3 minutes in PBS; vi. After PBS is removed, the 12-well plate with coverslips and fixed cells can be stored at -20° C. (up to 3 months). When left with PBS, the plates with coverslips and fixed cells can be stored in a refrigerator for up to 2 weeks, secured with a parafilm.

Blocking non-specific antibody binding: Add 1 ml of blocking buffer to wells containing slides with fixed cells and incubate for 1 hour. Preparation of the wet chamber: i. Prepare the container (e.g. Petri dish-15 cm); ii. Place the paper towel in the container and moisten it with water; and iii. Place a layer of Parafilm on the moistened paper towel. Preparation of dilutions of primary antibodies: i. Dilute antibodies in blocking buffer according to the following list:

Monoclonal Anti-Dystrophin antibody 1:200
Monoclonal Anti-Desmin antibody 1:100
Monoclonal Anti-Myosin (Skeletal, Slow) antibody 1:100

Labeling cells with primary anti-Dystrophin/Desmin/Myosin antibodies: i. Apply about 25-40 μl of the antibody dilution on the parafilm surface in the wet chamber leaving gaps allowing for covering the drops with coverslips later. ii. Cover the droplets of antibodies with coverslips in such a way that the surface of the coverslip covered with the cells has direct contact with the antibody. iii. Incubate overnight at 4° C. iv. After the incubation time has ended, transfer the coverslips back to a 12-well plate. Make sure that the surface of the coverslip covered with cells is directed upwards. v. Rinse the wells with PBS, three times. f. Labeling with secondary antibody: i. Prepare 0.5 ml of diluted secondary antibody for each well by diluting the Secondary antibody goat anti-mouse (FITC) 1:500 in PBS. ii. Add the 0.5 ml of diluted secondary antibody to the wells containing coverslips with cells labeled with primary antibodies. iii. Incubate for 1 hour at room temperature. iv. Rinse the wells with PBS, three times.

Mounting: i. Apply a single drop of Fluoroshield with DAPI on a microscope slide and cover each drop with one coverslip, so the surface of the coverslip with cells is facing down (is in contact with the Fluoroshield), ii. Wait for Fluorshield with DAPI to set; iii. Secure the edges of the coverslips with clear nail polish (optional). h. Analyze the microscope slides using fluorescence microscope.

Example of assessment of cell count and viability. Check the cells for viability on every passage, adding Trypan Blue to samples collected for cell counting. The Trypan Blue dye test is used to determine the number of viable cells present in a cell suspension. While live cells with intact cell membranes does not stain with Trypan Blue, the dead or damaged cells are stained blue. The cell counter can therefore recognize the live cells and dead cells and count them.

Equipment, reagents, materials and accessories: i. Serological pipette, 1-10 ml; ii. Automatic pipette with a range of 0.1-10 μl; iii. Pipette tips with a range of 0.1-10 μl, sterile; iv. Countess™ Cell Counting Chamber Slides (Invitrogen, 100078809); v. Trypan Blue stain 0.4% (Invitrogen, T10282) (previously prepared as 10 μl aliquots in 0.5 ml eppendorf microtubes). The procedure is as follows: a. Pipette the cell suspension several times using a serological pipette to make sure that the cells would be suspended evenly. b. Using a automatic pipette take a 10 μl sample of the cell suspension and add it to a 10 μl aliquot of Trypan Blue. Mix well but gently, and transfer the 10 μl of mixture into the Countess cell counting chamber slides. c. Immediately insert the Countess cell counting chamber slide into the Countness II counter (Invitrogen). The Countess II counter reports the cell count in 1 ml of suspension as well as the cell viability based on Trypan Blue staining. d. The cell count in 10 ml* of cell suspension is the number of cells counted by Countess II, multiplied by 10*. *If the cells were suspended in different volume of culture medium, multiply by appropriate number of ml.

In certain embodiments, a hemocytometer is employed cell count and viability (e.g., ADAM MC automated cell counter used according to the manufacture's instructions).

6. Myoblasts Labeling

Prior to the fusion protocol below, the donor and MD cell lines are labeled with different labels, such as with a stain, such that chimeric cells that are formed during fusion that contain both labels can be sorted away from other cells. Any type of suitable label or stain may be used if it allows the identification and isolation of the myoblast chimeric cells (MCCs).

Exemplary Staining Protocol:

This exemplary staining protocol is for staining a maximum $20 \times 10^6$ cells. 2 mL of Diluent C will be used with 4 μL of stain. For cell counts greater than $20 \times 10^6$ cells, calculate amounts accordingly. Also, this procedure utilizes minimal washing as to minimize the loss of cells prior to fusion. Alternatively, the manufacturer's protocol may be followed for staining purposes.

The protocol is as follows. Place cells obtained from above in a 50 mL conical tube and spin at 1410 rpm for 5 minutes. The cells will remain in the same 50 mL conical tube throughout staining and fusion protocols. Pour off supernatant. Spin for 1 minute to easily aspirate remaining supernatant. Leave no more than 25 μL of supernatant. Immediately prior to staining, prepare a 2× Dye Solution (4×10-6 M) in Diluent C by adding 4 μL of the PKH26 ethanolic dye solution (Catalog Number P9691) to 1 mL of Diluent C in an Eppendorf tube and mix well to disperse. Do the same for PKH67. Prepare a 2× Cell Suspension by adding 1 mL of Diluent C (Catalog Number CGLDIL) to the cell pellet and resuspend with gentle pipetting to ensure complete dispersion. Do not vortex and do not let cells stand in Diluent C for long periods of time. The PKH26 ethanolic dye solution should not be added directly to the cell pellet. This will result in heterogeneous staining and reduced cell viability. Rapidly add the 1 mL of 2× Dye Solution to 1 mL of 2× Cell Suspension and immediately mix the sample by pipetting. Incubate the cell/dye suspension for 5 minutes with periodic mixing. Stop the staining by adding 15-20 mL of sterile 1% BSA or human albumin and incubate for 1 minute to allow binding of excess dye. Fill remaining space in conical tubes with any complete media consisting of at least 10% FBS or human platelet lysate solution. Invert the tubes a couple of times to allow the media and cells to disperse throughout the tube. Centrifuge conical tubes at 1410 rpm for 5 minutes.

Pour the supernatant and resuspend the conical tubes in 20 mL DMEM+AA. Take a sample for counting and assessing viability and a sample for stained controls. Stained control should be pipetted into test tube with cell strainer. Dilute the stained control with at least 100 uL sorting buffer. Take up one of the resuspended, stained samples and mix it with the other stained sample. Rinse the now empty falcon tube with another 10 mL of DMEM+AA to assure all cells have been taken up. Take a sample for counting and assessing viability. Centrifuge conical tube at 1410 rpm for 5 minutes. Pour supernatant. Spin for one minute to easily aspirate remaining supernatant into test tube with cell strainer for mixed control. Leave no more than 25 μL of supernatant. The mixed cell pellet should be as dry as possible. Dilute the mixed control with at least 100 μL sorting buffer.

7. Fusion of Donor and MD Myoblasts

The fusion of the donor and MD myoblasts can be conducted in accordance with procedures known in the art (see, e.g., US Pat. Pub. 20180221416; Siemionow et al., Stem Cell Reviews and Reports (2018), 14:370-384; and Siemionow et al., Stem Cell Reviews and Reports (2018), 14:189-199; all of which are herein incorporated by reference in their entireties). In certain embodiments, the fusion protocol employs polyethylene glycol (PEG) at a concentration of 0.6-1.5 g/ml or 1.0-1.3 g/ml (e.g., 1.0 . . . 1.1 . . . 1.2 . . . or 1.3 g/ml). In other embodiments, the fusion is conducted for no more than 8 minutes. In further embodiments, the fusion is conducted such that at least 40%.

Exemplary Fusion Protocol:

The cell-fusion solution is prepared as follows. 1) 3.0 g PEG is put into 2 mL DMEM+1% Antibiotic and allowed to sit in a warm bead bath/water bath at 37° C. until the PEG is fully dissolved and into solution. 2) Once a homogenized solution is obtained, 400 μL of DMSO is added. 3) The entire solution is filtered through a needle filter into a new sterile tube to sterilize it. 4) The PEG solution is now ready for fusion procedure.

Staring with the cell pellet from the exemplary staining protocol above, dislodge pellet by gently "tapping" 50 mL conical tube against the surface of the hood. Cells should be distributed around the bottom of the tube (angled part of tube). Very slowly and carefully add 500 uL of PEG solution. The addition of PEG solution should be within 1 s or 30 s time. Start the timer as soon as the PEG is introduced to the cells. Rotate the tube to expose all cells to the PEG. After adding the PEG rotate the tube within additional 30 s. After this 1 minute (30 s+30 s) time, move the tube into a 37° C. thermoblock set for 300 rpm. Quickly spray the tube with ethanol and wipe before reintroducing the tube to the sterile hood. After 1 minute incubation, add 1 mL of DMEM+AA (serum-free media) while rotating the tube over a 1 minute time span. Add 15 mL of DMEM+AA over a 3 minute period. Take a 5 mL serological pipet and take up 5 mL of DMEM+AA. Add 5 mL over a 1 minute time span and repeat 2 more times. This will assure slow addition. After the 15 mL addition, fill remaining space with complete media composed of at least 10% FBS or 20% human platelet lysate solution to stop the PEG reaction. Invert the tube several times to assure medium is distributed throughout and take a sample for counting pre-sort and assessing viability. Centrifuge at 1410 rpm for 5 minutes. Carefully pour the supernatant out and the fusion is complete. The cells should be resuspended in approximately 10 ml of complete medium. It is noted that one should not pipet up and down when performing fusion. Rotate, swirl, and/or invert to place cells into PEG and media.

8. Sorting Myoblast Chimeric Cells (MCCs)

The sorting of generated MCCS can be conducted in accordance with procedures known in the art (see, e.g., US Pat. Pub. 20180221416; Siemionow et al., Stem Cell Reviews and Reports (2018), 14:370-384; and Siemionow et al., Stem Cell Reviews and Reports (2018), 14:189-199; all of which are herein incorporated by reference in their entireties). An exemplary protocol is as follows.

Exemplary MCC Sorting Protocol

For this exemplary sorting procedure both the suspension of cells after Fusion and a small sample (1M of cells) of MIX should be prepared (in separate Cartridges). The double positive stained cells (PKH26+/PKH67+) sorted into the Positive Chamber of the sorting Cartridge will be referred to as MCCs. Equipment, reagents, materials and accessories as follows: a. Equipment: i. Falcon tubes, 50 ml, ii. Pre-separation filters 20 µm (Miltenyi, 130-101-812), iii. MACSQuant Tyto Cartridges (Miltenyi, 130-106-088) iv. MACSQuant Tyto magnetic stand for cartridges, v. Serological pipettes, vi. Sterile pipette tips, vii. Sterile, microcapillary pipette tips, viii. KD-Ject III Syringe, 10 ml (KDM, 831939), ix. Cell counting Chamber slides (Invitrogen, 100078809); b. Reagents: i. MACSQuant Tyto Running Buffer (Miltenyi, 130-107-207), ii. PBS without Ca/Mg, sterile, iii. Cell culture medium, iv. Trypan Blue stain 0.4% (Invitrogen, T10282); c. Accessories: i. Medical gloves, ii. Disinfectant liquid, and iii. Disposable, lockable container.

The preparation of cells for the sort should be proceeded as follows: a. Centrifuge the suspension of cells at 1410 rpm, 10 min. b. Remove and discard the supernatant. c. Resuspend the cells in the desired volume of sorting buffer. d. Cartridge preparation should be proceeded as follows: i. Remove the Input Chamber screw cap. ii. Add 200 ul MACSQuant Tyto Running Buffer to the Input Chamber using a microcapillary pipette tip. iii. Place the cartridge on the magnetic stand to open the valve and thereby allow the liquid to flow into the Positive Chamber. iv. Pull back the plunger of the syringe, and then screw the syringe to the Input Chamber. v. Press the air with the syringe plunger until you see the liquid on the whole surface of the Positive Chamber bottom. vi. Remove the cartridge from the magnetic stand. vii. Gently continue to press the air within the syringe. Pay attention to not let the plunger retract. viii. Ensure that the liquid covers the bottom of both the Input Chamber, Positive Chamber and Negative Chamber. ix. Unscrew the syringe and remove its plunger. Make sure that the plunger seal stays sterile. e. Screw the syringe barrel into the Input Chamber. f Rinse the pre-separation filter with sterile PBS. Remove excess PBS. g. Place the pre-separation filter in the syringe inlet. h. Using a pipette (serological or automatic, depending on the volume of the cell suspension), filter the cells through a pre-separation filter. i. Tap the pre-separation filter several times to collect the sell suspension that could remain on the bottom layer of the filter. j. Remove the pre-separation filter. k. Gently place the plunger back in the syringe barrel. l. Gently press the syringe plunger until the cell suspension will be transferred into the Input Chamber. m. Unscrew the syringe, turn the syringe "tip up" and carefully press the plunger to remove the excess air and collect the cell suspension adhering to the inside walls of the syringe barrel. n. Screw the syringe to the Input Chamber. Transfer the remaining cell suspension into the Input Chamber. o. Unscrew the syringe. p. Close the Input Chamber opening with its screw cap. After the preparation of cells for the sort is finished and cells suspended in the Tyto Running Buffer are loaded into the Input Chamber of the MACSQuant Tyto cartridge the sorting procedure should be proceeded as follows: a. Turn on the MACSQuant Tyto Sorter. b. Launch the MACSQuant Tyto Sorter software. c. Open the "MCC Sorting template" workspace. After any adjustment to the template remember to save the workspace adding the current date to the name. d. Insert the Cartridge with the sample of MIX according to the MACSQuant Tyto Sorter instruction. e. Start the flow of cells without sorting. f. Monitor the histograms displaying the signal from the PKH26 (channel B2) and PKH67 (channel B1) and the P1 gate (FSC vs SSC). g. Select the channel on which a more intense signal is observed. Set gates on histograms. h. The channel with the dominant signal will be the channel for the further trigger and threshold settings i. Set the gate on the PKH26 vs PKH67 plot. Sorting gate should not include single stained cells and should be focused on double positive PKH26+/PKH67+ cells (not present in MIX). j. Stop the cells flow. k. Remove the Cartridge with MIX. 1. Insert the Cartridge with cells after the Fusion. m. Use the settings prepared on the MIX. n. Start the sort. o. Adjust the settings if necessary. p. Take a screenshot of the process at the beginning and at the end of each sort by pressing PrtScr key on the keyboard. The Screenshot would be saved automatically. q. The parameters of the sorting process should be as follows: i. Pressure <150 mbar (optimally <120 mbar), ii. Abort rate for 60 min <5%, iii. Sort rate <300 events/s. r. Monitor the sorting process for any disturbances to ensure that in the case of any malfunction the sorting process could be stopped and/or corrective actions would be taken: i. If the sorter is recording sorting events, but the sorting valve visible on the touchscreen is not moving and the flow of cells sorted to the Positive Chamber are not visible use the Free Valve option to force the valve movement and to check if its not clogged. ii. If the Free Valve option does not unblock the valve, the sort should be stopped and the Cartridge removed (the cells could be recovered and the sort repeated in the new Cartridge). iii. If the sort rate is above 300 events/s and the pressure is above 150 mbar stop the sort, remove the Cartridge, transfer the cell suspension to sterile tube, dilute with running buffer and try sorting again in the new Cartridge. 5. After the sorting process ends the procedure is as follows: a. Remove the cartridge from the MACSQuant Tyto Sorter and bring it back to the laminar chamber. b. Remove the Positive Chamber screw cap. c. Transfer the cells (MCC) suspension from the Positive Chamber with automatic pipette and microcapillary pipette tip to the new sterile tube. d. Add about 200-300 µl of cell culture media to the Positive Chamber to collect any remaining (MCC) cells and transfer the content to the sterile tube with MCC cells collected before. e. Collect a sample for cell counting: Collect 10 µl of MCC cell suspension and mix it with 10 µl of the Trypan Blue stain. Transfer to the Cell counting Chamber slide. Measure the cell count and viability using Countess II Cell Counter. f. After the cell count and viability is known calculate the right volumes of cell suspension for each Quality Control and collect them.

9. MCC Cells Expansion

After the MCCs are created and sorted, they are expanded to create a final population of expanded MCC cells (e.g., expanded to at least 50 million . . . at least 100 million . . . or at least 300 million MCCs). In certain embodiments, the cells are tested before and/or after each expansion to ensure they meet all or at least some of the criteria described below. In certain embodiments, the MCCs are tested before and/or after expansion to ensure CD56 expression is at least 40%.

In particular embodiments, the MCCs are passaged when the cells are at about 70-75% confluence. In general, confluence of above 80% (or above 75%) is avoided to avoid/prevent spontaneous differentiation into myotubes. In certain embodiments, the MCCs are only passaged (e.g., 75% confluent and adherent MCCs are treated with cell dissociation agent and transferred to new container with new media) one, two, three, or four times before packaged in a container for later administration to a human (e.g., to treat MD in a patient). In certain embodiments, the MCCs are passaged two or three times before being packaged for later human administration. An exemplary MCC cells expansion protocol is provided below.

Exemplary MCC Cell Expansion Protocol:

The following quality control criteria should be checked on each passage, as long as the number of collected cells is sufficient (for quality control about 2M of cells should be collected).

i. Morphology of cultured cells;
 ii. Confluency of cultured cells (e.g., at least 60-80% or 65-80% confluency reached);
 iii. Cell Count & Viability (e.g., using Trypan Blue; greater than 80% or 90% viable);
 iv. CD34/CD45 (less than 10% or less than 5% expression; tested by FACS) & CD56/CD90 (greater than 6050% or greater than 7050%; tested by FACS)
 v. Desmin (immunolocalization greater than 60% or 70% in the intracellular fluid) & Dystrophin (immunolocalization greater than 60% or greater than 70% in the intracellular fluid).

The following should additionally be checked on passage p1→p2:

i. MyHC (myosin heavy chain expression in intracellular fluid) preferably less than 15% or less than 10%)
 ii. Differentiation index (Pappenheim stain; at least 30% or at least 40%)
 iii. PCR-STR (Short Tandem Repeats) analysis of MCC for presence of parent cell specific loci from both donors.
 iv. Karyotype (to assess normal karyotype of myoblast parent cells before fusion and confirm normal karyotype in MCC (e.g. lack of chromosome aberrations). The MCC culture process is as follows. After the fusion process, seed the appropriate number of MCC (Table 2) into a new culture vessel.

TABLE 2

| The seeding density of MCC | |
| --- | --- |
| Culture vessel | Cell number |
| T25 | 50-150k |
| T75 | 150-300k |
| T225 | 0.5-1mln |
| T525 | 1-4mln |
| T875 | 4-8mln |

The confluence of the bottle should be monitored daily. MCC should be passaged when about 60-80% confluency is reached. MCC should be passaged if cells starts to aggregate or the confluency reaches 75% in some areas of the growth area. The culture medium should be changed at least once a week, and the FGF should be supplemented to the medium every 2-3 days (e.g., Monday, Wednesday, Friday).

MCC expansion is as follows. MCC culture may be expanded using the appropriate culture vessels and volumes of medium, according to the Table 1.

TABLE 1

| The volumes of liquids used in cell culture depending on the size of culture vessel. | | | | |
| --- | --- | --- | --- | --- |
| Culture vessel | PBS | Detachment solution (TrypLE) | Medium | FGF |
| T25 | 2-4 ml | 2 ml | 5 ml | 1.2 ul |
| T75 | 3-10 ml | 5 ml | 15 ml | 3.6 ul |
| T150 | 5-20 ml | 10 ml | 30 ml | 7.2 ul |
| T225 | 10-30 ml | 15 ml | 50 ml | 12 ul |
| T525 | 15-40 ml | 20 ml | 90 ml | 21.6 ul |
| T875 | 25-60 ml | 30 ml | 150 ml | 36 ul |

MCC passage should proceed as follows. Before the passage: i) Insert complete medium, PBS and detachment solution (TrypLE) into a water bath (set at 37° C.) or thermostat one hour before starting work; ii) TrypLE reagent is ready to use If using 10× detachment solution, dilute the product 10 times by taking 10 ml 10× detachment solution into a sterile bottle and adding 90 ml PBS without Ca/Mg ions. The passage procedure is as follows: i) Remove the culture medium from culture flask by pouring it into a sterile container. ii) Wash the cells twice with sterile, preheated PBS without Ca/Mg ions. The PBS should be added to the vessel with a sterile serological pipette. The added volume of PBS depends on the culture Flask used and should be measured according to the Table 1. PBS should be poured discarded into a sterile container. iii) Add the appropriate amount of previously prepared, pre-warmed TrypLE (or other cell detachment agent) to the cells washed previously with PBS. The added volume of TrypLE depends on the culture vessel used and can be measured according to Table 1. iv) The cells should be incubated with TrypLE for 3-7 minutes at room temperature or in incubator at 37° C. The detachment of the cells from the bottom of the vessel should be monitored under a microscope every 2 minutes.

If necessary, gently tap the vessel several times in order to detach the cells, however the incubation time of 3-7 minutes should not be exceeded, as this may affect the cell viability. v) After the cells detachment TrypLE (or other detachment agent) should be neutralized with culture medium by adding the volume of culture medium equal to the double volume of trypsin used. vi) Transfer the cell suspension to 50 ml sterile Falcon tube(s). vii) Centrifuge cells for 5 min at 1400 rpm, RT. viii) Gently remove the supernatant from the pellet using a sterile serological pipette. ix) Resuspend the pellet in 2-10 ml of culture medium using sterile serological pipette depending on the expected cell count. x) Count the cells with hemocytometer or accordingly to the cell counter manufacturer protocol (i.e. ADAM MT cell counter) If using Countess Cell counter Take a 10 μl sample of the cell suspension and add it to a 10 μl aliquot of Trypan Blue. Mix well but gently, and transfer the 10 μl of mixture into the Countess cell counting chamber slides. xi) Immediately insert the Countess cell counting chamber slide into the Countness II counter (Invitrogen). The Countess II counter reports the cell count in 1 ml of suspension as well as the cell viability based on Trypan Blue staining. xii) The cell count in 10 ml* of suspension is the number of cells counted by Countess II, multiplied by 10*. *If the cells were suspended in different volume of culture medium, multiply by appropriate number of ml. xiii) Calculate the appropriate volume of cell suspension to be seeded or collected for the Quality Control, according to the formula: $z=L*10/x$, where X—cell count in 10 ml; where L—number of cells to be passaged; Z—the volume of suspension with L cells. xiv) Collect the samples for Quality Control (if needed). xv) Knowing the cell count choose the culture vessel and add the appropriate volume of culture medium, according to the Table 1 and Table 2. xvi) Add the appropriate volume of cell suspension (calculated in step 4.b.xiv.) to a new culture vessel with culture medium. Make sure that the cells are suspended evenly in the culture medium by pipetting several times or gently moving the vessel. xvii) Make sure that the medium is distributed evenly on all the growth area(s) of the vessel. xviii) Sign the vessel with: Cell line ID, passage, date, number of cells seeded. xix) Place the vessel in the incubator.

10. MCC Cells Qualification and Product Preparation

After the MCCs have been produced and expanded as described above, in some embodiments, they are tested to ensure certain criteria are met. In certain embodiments, the cells are examined to determine that there are at least 100 million cells in each cell line (e.g., at least 100 . . . 150 . . . or 200 million or 300 million or 400 million). In other embodiments, the cells are examined to ensure at least 80% viability (e.g., at least 80% . . . 85% . . . or 90% viability). In certain embodiments, the cells are tested to ensure that they have less than 10% (e.g., less than 10 . . . 7 . . . or 5%) of CD34 and/or CD45 expression. In some embodiments, the cells are tested to ensure that they have at least 50% or 60% (e.g., 60% . . . 65% . . . 70%) of CD56 and/or CD90 expression. In particular embodiments, the cells are tested to ensure they have at least 50% or 60% (e.g., 60% . . . 65% . . . 70%) desmin (DES) protein expression and/or dystrophin expression.

In certain embodiments, after the MCCs have been produced and expanded, they are tested to ensure that, upon expansion, the level of cells containing a dye (e.g., which may not be approved for human administration) is present in less than 97% or less than 99% of the MCCs (e.g., less than 97% . . . 98% . . . 98.5 . . . 99% or 99.8%).

In work conducted during development of embodiments herein, the level of two dyes, PKH26 and PKH67, were measured after initial MCC generation, the first passage, and the second passage. The fluorescence levels are presented in the FIG. 4, and exemplary data presenting the FACS dots plots from PKH26/PKH67 fluorescence are presented in the FIG. 5.

Figure 4:
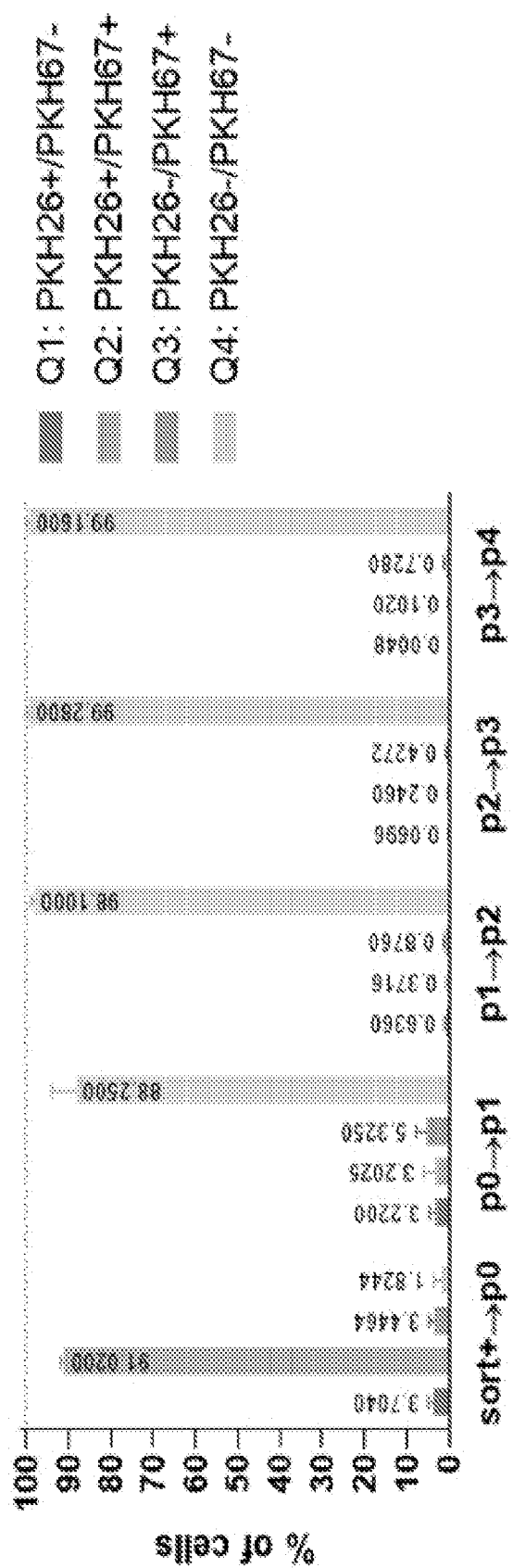
FIG. 4 shows the fluorescence level of PKH26 and PKH67 measured by FACS in parental and MCC cell cultures at subsequent passages.
Figure 5:
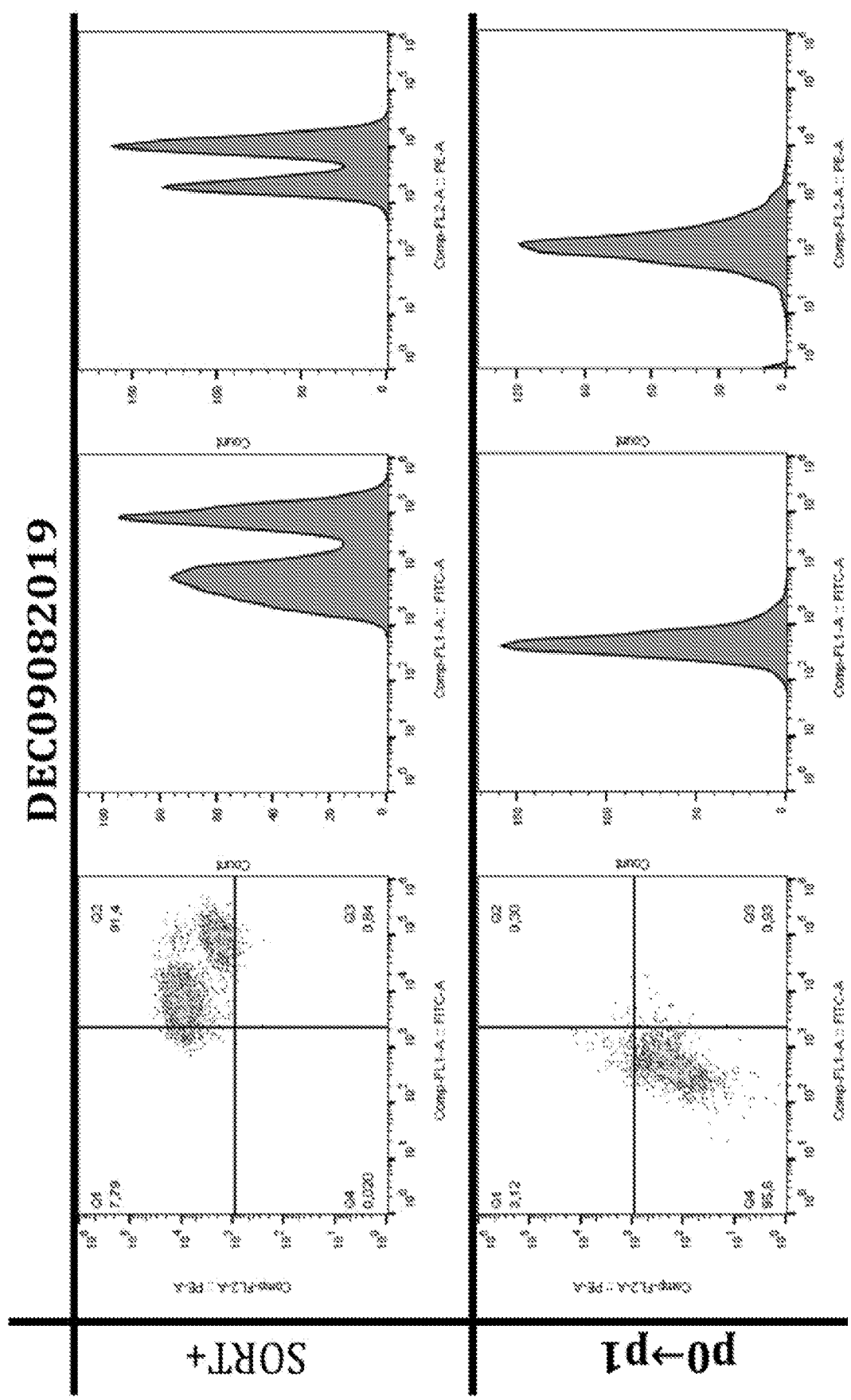
FIG. 5 shows exemplary FACS dot plots presenting the fluorescence of PKH26 and PKH67 in cell culture at different passages.
Figure 5:
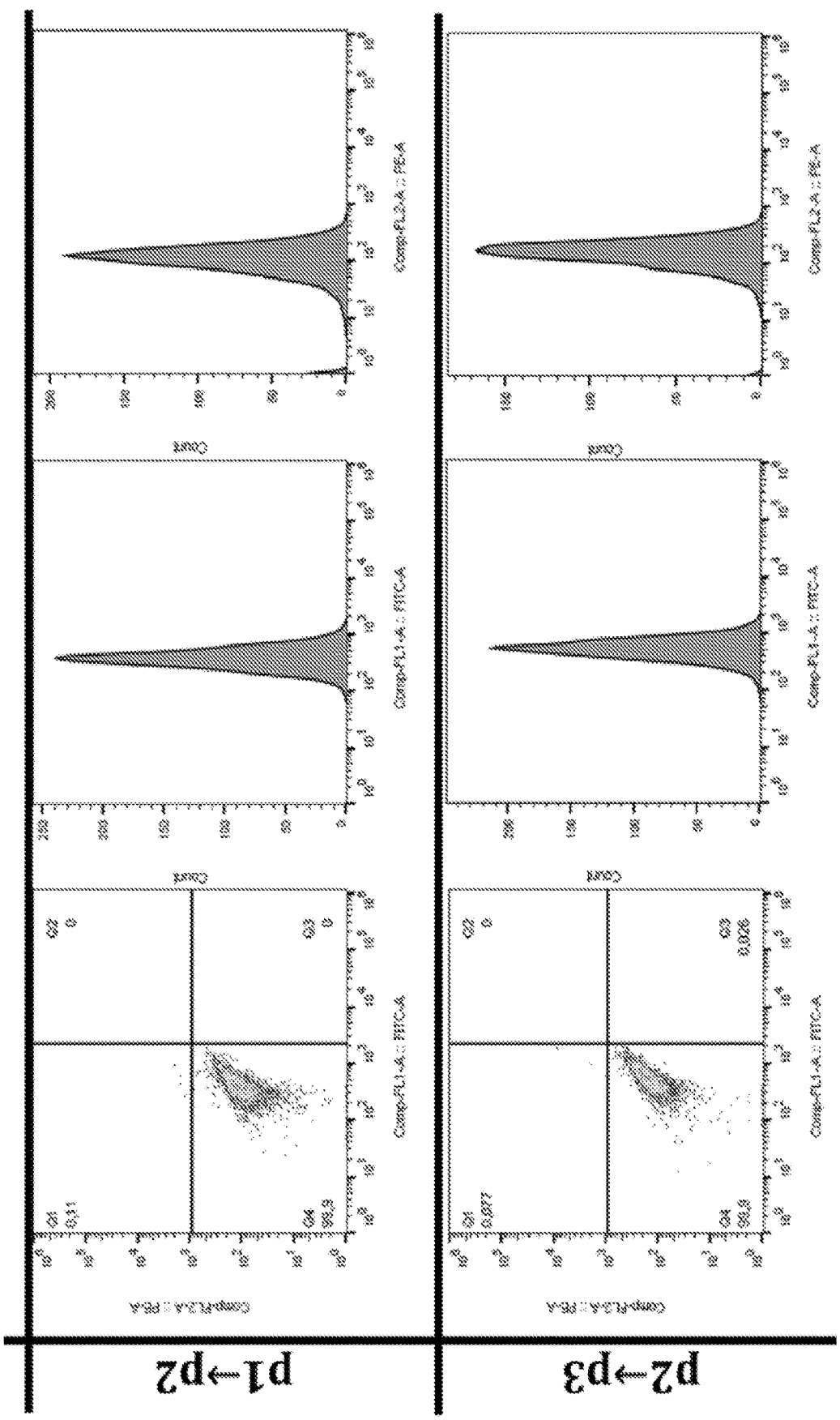
Figure 5:
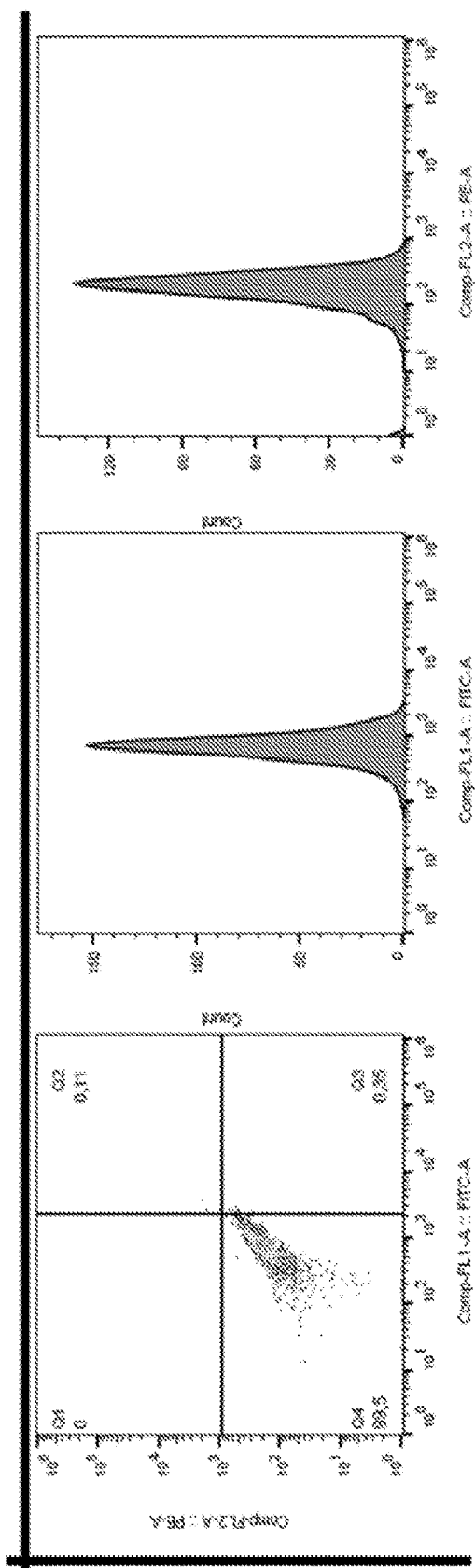

As shown in FIG. 4 The number of fluorescent cells directly after MCC sorting as a positive sort (sort+) is as follows:

91% cells express the fluorescence of PKH26/PKH67
3.7% cells express the fluorescence of PKH67
3.4% cells express the fluorescence of PKH26
The number of fluorescent cells at p0→p1:
3% PKH26+/PKH67+ cells
3% PKH26+ cells
5% PKH67+ cells
88% of cells that are negative for both PKH26 and PKH67
The number of fluorescent cells at p1→p2 and later
98-99% cells are negative for both the PKH26 and PKH67
1-2% cells in total are positive either for PKH-67 or PKH26.

After the MCC expansion in vitro is finished the cells are detached (e.g., trypsinized), collected and prepared for the final product preparation. The procedure proceeds as follows. Samples of culture medium from the MCC culture will be collected for the Quality Control. MCC are washed with PBS detached for up to 5 minutes, collected to the sterile. 50 ml Falcon tubes. The culture vessel is washed with culture medium to collect any remaining cells. The medium (with cells) is collected and added to the Falcon tubes with the suspension of cells to neutralize the detachment solution. The Falcon tubes with MCCs are centrifuged at 1410 rpm. for 5 minutes. The supernatant is discarded and the cells pellets are resuspended in the transport medium (i.e. sterile saline 0.9% NaCl). The samples for cell counting and Quality Control are collected.

Appropriate number of MCC cells (depending on the dosage calculated in reference to the patient body weight in kilograms i.e. $2\times10^6$ cells per kilogram body weight, $4\times10^6$ cells per kilogram body weight, $6\times10^6$ cells per kilogram body weight) is to be resuspended in the appropriate volume of transport medium in ml (calculated with respect to the final $20\times10^6$ cells/ml density of the final product) are transferred to the sterile vials (i.e. 2 ml or 5 ml CellSeal vials can be used—depending on the final volume of the product) equipped with adequate label. The product is stored at 2-8° C. until the results of the endotoxins test are known. The labeled container with the product is placed in passive temperature controlled packaging (2° C.-8° C.), together with a temperature logger and filling assuring proper position of the transport vial. The passive temperature controlled packaging (ORCA) will be closed and labeled. The packaged product is transported to the hospital via medical transport. In general, the product should be used to treat a subject with a muscle disease within about 12 hours.

11. Dosage and Administration to Treat Subject with MD

The final prepared and tested MCCs are administered to a subject to treat MD. The MCCs can be administered by engraftment, wherein the cells are injected into the subject, for example, intravenously, intra-muscularly, intra-arterially, intra-bone and the like. In certain embodiments, administration involves engrafting about $10^2$, $10^4$, $10^6$, $10^7$, $10^8$, $10^9$, or more cells. The number of cells engrafted may be chosen based on the route of administration and/or the severity of the condition for which the cells are being engrafted. Such treatment is intended to engraft and complement the function of defected muscles of muscular dystrophy patients.

Compositions containing the MCCs can be prepared by combining the cell or combination of cells with a pharmaceutically acceptable carrier or aqueous medium. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes solvents, dispersion media, coatings, antibacterial and antifungal agents, isotonic and the like. The use of such media and agents for pharmaceutically active substances is well known in the art. Except insofar as any conventional media or agent is incompatible with the cells of the present disclosure, its use in therapeutic compositions is contemplated. Pharmaceutical compositions can be determined by one skilled in the art depending upon, for example, the intended route of administration, delivery format and desired dosage. See, for example, REMINGTON'S PHARMACEUTICAL SCIENCES, 18th Edition, (A. R. Gennaro, ed.), 1990, Mack Publishing Company.

The MCC containing compositions of the invention can be incorporated in an injectable formulation. The formulation may also include the necessary physiologically acceptable carrier material, excipient, lubricant, buffer, surfactant, antibacterial, bulking agent (such as mannitol), antioxidants (ascorbic acid or sodium bisulfite) and the like. Acceptable formulation materials preferably are nontoxic to recipients at the dosages and concentrations employed. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials may include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA; complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as PLURONICS, PEG, sorbitan esters, polysorbates such as polysorbate 20 and polysorbate 80, TRITON, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, REMINGTON'S PHARMACEUTICAL SCIENCES, Id.

The primary vehicle or carrier in a pharmaceutical composition may be either aqueous or nonaqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical compositions can comprise Tris buffer of about pH 7.0-8.5, or acetate buffer of about pH 4.0-5.5, which may further include sorbitol or a suitable substitute therefore. Pharmaceutical compositions of the invention may be prepared for storage by mixing the selected composition having the desired degree of purity with optional formulation agents (REMINGTON'S PHARMACEUTICAL SCIENCES, Id.) in the form of a lyophilized cake or an aqueous solution.

The MCC containing compositions can be provided by sustained release systems, by encapsulation or by implantation devices. The compositions may be administered by bolus injection or continuously by infusion, or by implantation device. The composition also can be administered locally via implantation of a membrane, sponge or another appropriate material onto which the cell or cells have been absorbed or encapsulated. Where an implantation device is used, the device may be implanted into any suitable tissue or organ. The injections may be given as a one-time treatment, repeated (daily, weekly, monthly, annually etc.) in order to achieve the desired therapeutic effect.

Cell encapsulation methodology has been previously described which allows transplantation of encapsulated cells in treatment of Parkinson's disease (Tresco, et al. (1992) ASAIO J. 38:17-23) or Amyotrophic lateral sclerosis (Aebischer, et al. (1996) Hum. Gene Ther. 7:851-860). In accordance with this embodiment, MCCs are encapsulated by compounds which form a microporous membrane. Capsules, for example approximately 1 cm in length, containing the cells of interest may be prepared employing a hollow microporous membrane fabricated from poly-ether-sulfone (PES) (Akzo Nobel Faser AG, Wuppertal, Germany; Deglon, et al. (1996) Hum. Gene Ther. 7:2135-2146).

The MCC containing compositions of the invention can be delivered parenterally. When parenteral administration is contemplated, the therapeutic compositions for use in this invention may be in the form of a pyrogen-free, parenterally acceptable aqueous solution. A particularly suitable vehicle for parenteral injection is sterile distilled water. Preparation can involve the formulation with an agent, such as injectable microspheres, bio-erodible particles, polymeric compounds (such as polylactic acid or polyglycolic acid), beads or liposomes, that may provide controlled or sustained release of the cell or cells, which may then be delivered via a depot injection. Formulation with hyaluronic acid has the effect of promoting sustained duration in the circulation. Implantable drug delivery devices may be used to introduce the desired composition.

The MCC containing compositions may also contain adjuvants such as preservative, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Supplementary active ingredients also can be incorporated into the compositions. The active compositions of the present disclosure may include classic pharmaceutical preparations.

As used herein, the term "amount effective," "effective amount" or a "therapeutically effective amount" refers to an amount of the cell or composition of the invention sufficient to achieve the desired result. The amount of the cell or composition which constitutes an "effective amount" or "therapeutically effective amount" may vary depending on the severity of the disease, route of administration (e.g., intra-bone) the condition, weight, or age of the patient to be treated, the frequency of dosing, or the route of administration, but can be determined routinely by one of ordinary skill in the art. A clinician may titer the dosage or route of administration to obtain the optimal therapeutic effect.

Exemplary Dosage and Administration Protocol

MCCs can be provided as a cell suspension for injection, enclosed in a ready-to-use, individually labelled, sterile vial. Single dose contains the number of cells depending on the dosage calculated in reference to the patient body weight in kilograms i.e. $2\times10^6$ cells per kilogram body weight, $4\times10^6$ cells per kilogram body weight, $6\times10^6$ cells per kilogram body weight. The appropriate number of cells is to be resuspended in the appropriate volume of transport medium in ml (calculated with respect to the final $20\times10^6$ cells/ml density of the final product) i.e. saline or saline supplemented with glucose or appropriate medium in order to provide favourable transport conditions for the cells. The procedure should be repeated and finally the cells should be suspended in the appropriate volume (in ml) of transport medium. The product prepared in this way will be ready for administration. Each dose will contain the appropriate number of MCCs cells, depending on the patient dosage regimen, suspended to the final density of $20\times10^6$ cells per ml in the appropriate volume of saline or saline supplemented with glucose or albumin, respectively of the body mass of the patient.

MCC cells suspension are for injections in the indication of Duchenne muscular dystrophy. The proposed route of administration is systemic by intraosseous delivery to hipbone-iliac crest. At the time of administration, patients will be under general anaesthesia and in addition topical anaesthetics (e.g., topical lidocaine at the site of infusion) may be administered to subjects, consistent with institutional guidelines. The intraosseous (IO) infusion should be administered by qualified healthcare professionals trained to detect any infusion related issues. Infusion times, rates, any infusion interruptions or infusion rate reduction, will be recorded. The MCC suspension should be infused under general anaesthesia or analgosedation/sedation based on anaesthesiologist decision over 30 minutes period where time 0 is the beginning of the infusion. The end of administration is defined by pulling the needle out of the participant's bone. Subjects should be observed for 1-hour following completion of the investigational product administration. The patient will be hospitalized 24 hours after administration of the product.

The following equipment is employed in this exemplary protocol: i) medullar cavity injection set (classic needle with a mandrin—Jamshidi needle), ii) sterile cotton swabs, sterile sling to protect the skin, skin disinfectant, iii) 1-2% lidocaine solution, needle and syringe (for local anaesthesis), sterile gloves, and iv) syringes—preferred capacity: 5 ml and 10 ml (preferably partially filled with NaCl solution or one empty—for aspiration and the other one—filled with saline for patency monitoring).

Injection technique to the bone marrow cavity and administration of the MCCs is as follows: i) The patient is positioned on his back on the operating table and subjected to general anaesthesia. ii) The injection site is selected. iii) The injection site is disinfected. iv) The needle should be inserted preferably at the right angle to the bone surface. A sudden loss of resistance should be felt during bone puncture (this is a signal that the needle passed through the compact bone and reaches the medullary cavity). The needle should be entered at a depth of about 1 cm from the bone surface. v) Remove the mandrin from the needle and verify the injection positioning. The following symptoms ascertain correct needle injection: a) blood flow from the needle, b) the possibility to aspirate blood or bone marrow with the syringe, c) undisturbed saline injection to the medullar cavity without the signs of oedema of surrounding tissues (otherwise it would be a sign that the tip of the needle is beyond the medullar cavity), and d) stability of the puncture position without the need for additional support. vi) Before administration of the MCCs, around 3-5 ml bone marrow shall be aspirated (in order to create the space for IMP administration) and transferred to the EDTA tube kept on dry ice. vii) The MCCs suspended in 5 ml saline shall be administered with the 5 ml syringe to the medullary cavity. viii) After MCC administration, the insertion site is secured with the bone wax and pressure applied for several minutes. ix) Upon completion of the MCC administration, the injection site is secured with non-occlusive dressing in order to observe associated tissues. The procedure takes approximately 30 minutes.

Each MCC cell suspension is packaged individually in a sterile vial (e.g., CellSeal 2 ml or 5 ml) or vials—depending on the number of cells and the final volume of the cell suspension. The suspension could be divided into more than one vial if needed, but as few vials as possible should generally be used. For example $100 \times 10^6$ cells with the density of $20 \times 10^6$ cells/ml are suspended in 5 ml of transport medium and packed in one 5 ml vial, while $20 \times 10^6$ cells with the density of $20 \times 10^6$ cells/ml are packed in one 2 ml vial and $200 \times 10^6$ cells with the density of $20 \times 10^6$ cells/ml are packed in two 5 ml vials.

12. Cryopreservation

Figure 6:
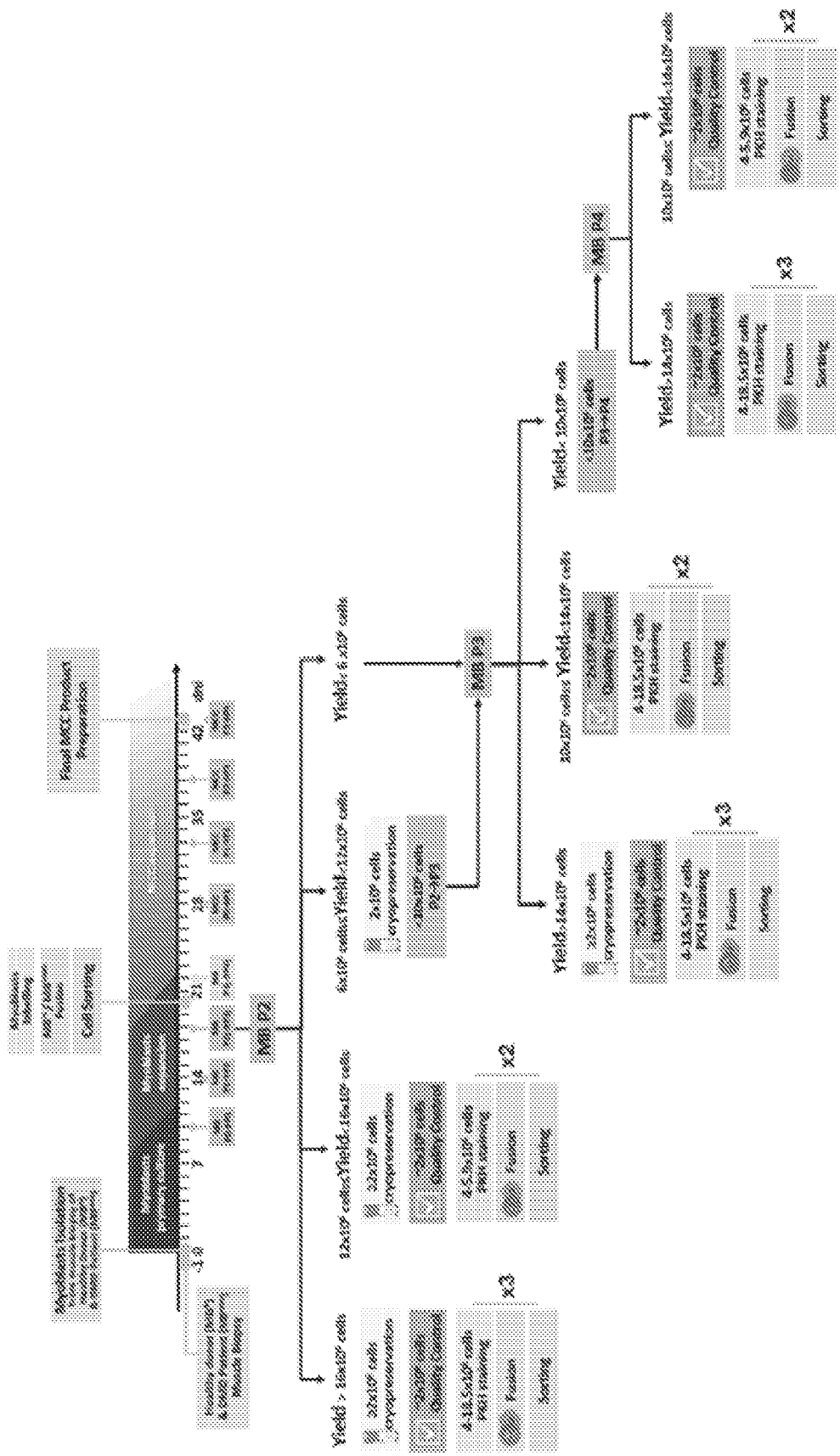
FIG. 6 shows an exemplary decision flowchart for cryopreservation and fusion of Myoblasts. The Figure describes an exemplary decision flowchart on how myoblasts (MB) are passaged and when myoblasts are cryopreserved or when fusion is performed. An important parameter is the MB Yield. In this chart, fusion and quality control are only performed when there is sufficient number of MBs. In this chart, if the MB yield is sufficient, surplus cells are cryopreserved. In most cases the MB Fusion is performed at passages P2 or P3 of MB culture, however in some cases the Fusion is performed at passage P4 or P5, as long as the cell yield is sufficient and meets the Quality Control criteria.
Figure 7:
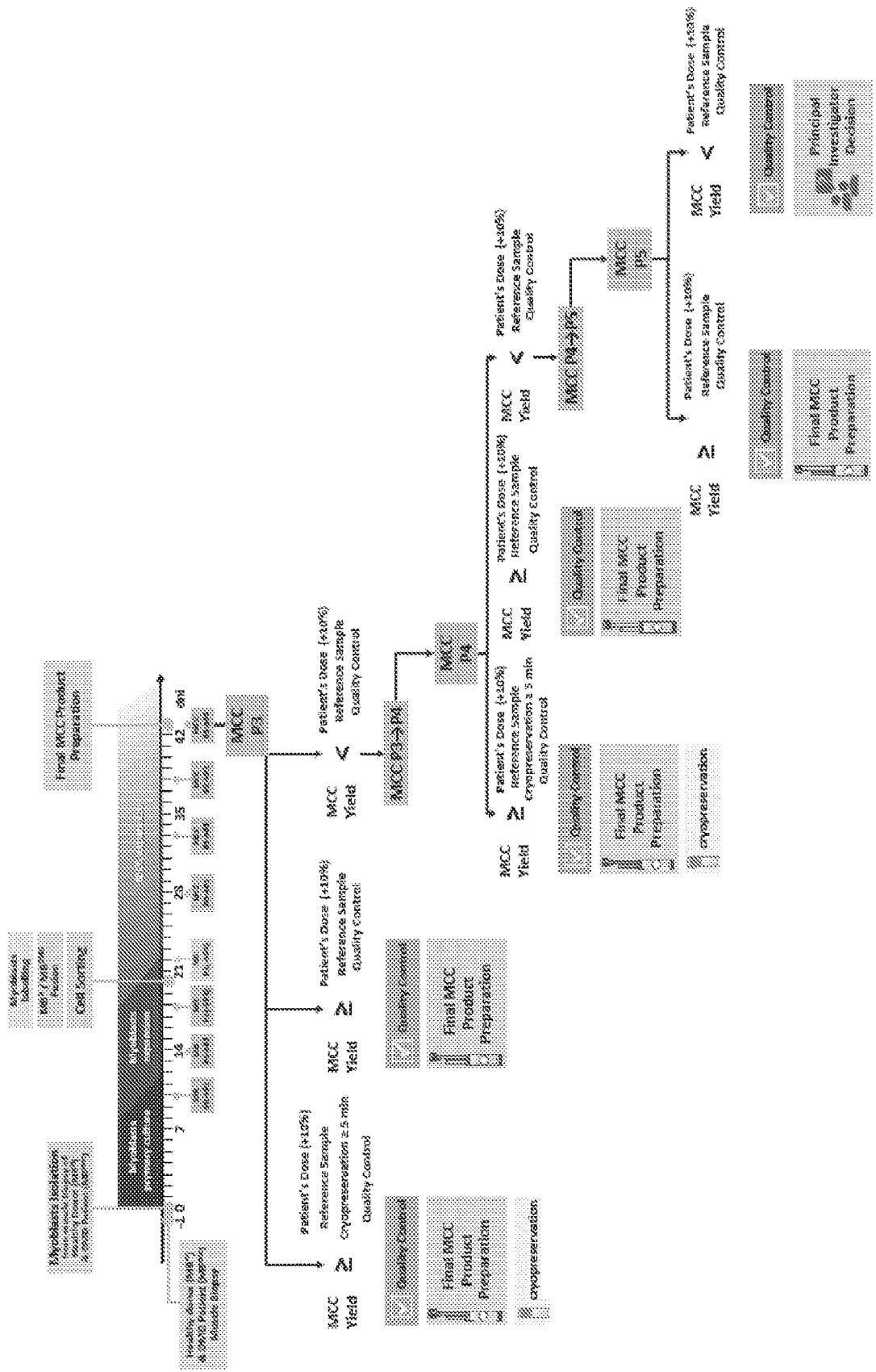
FIG. 7 shows an exemplary decision flowchart for cryopreservation and final MCC Product Preparation. This figure describes an exemplary decision flowchart on how MCCs are passaged and when MCCs are cryopreserved or when Final MCC product is prepared. One of the most important parameters is the MCC Yield. In this chart, when MCCs are in sufficient number, they are harvested for the preparation of Final product as well as Quality Control. If the MCCs Yield is sufficient, surplus cells are cryopreserved. In most cases the MCC Final Product is prepared at passage P3 or P4 of MCCs culture, however in some cases the MCC Final Product could be prepared at passage P2 or P5, as long as the Cell Yield is sufficient and meets the Quality Control criteria.
Figure 8:
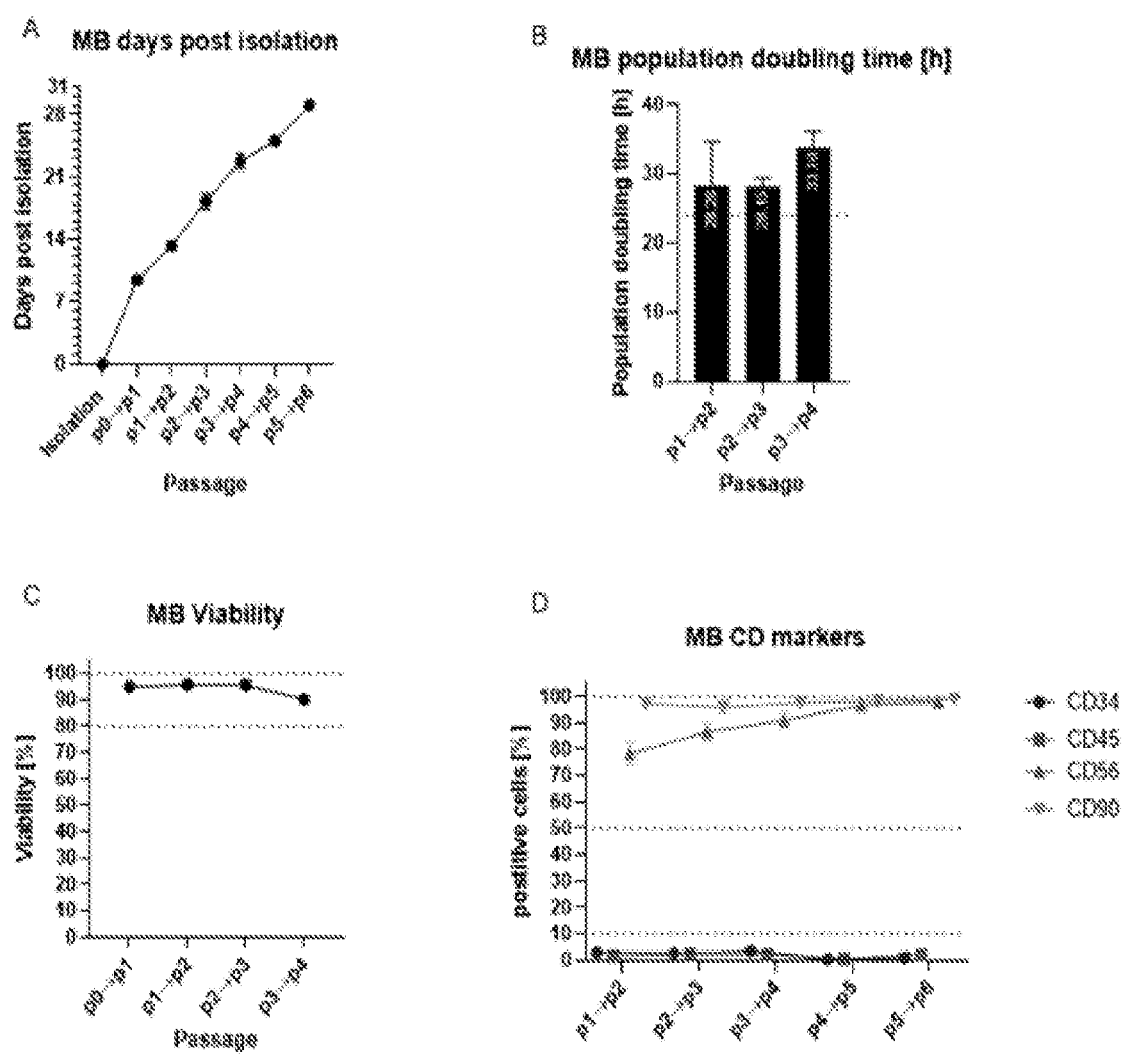
FIG. 8 shows results generated in work conducted during development of embodiments of the present disclosure. In particular.
Figure 9:
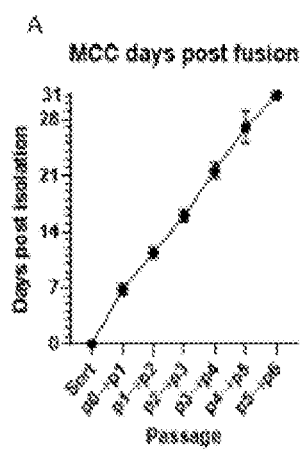
FIG. 9 shows results generated in work conducted during development of embodiments of the present disclosure. In particular.
Figure 9:
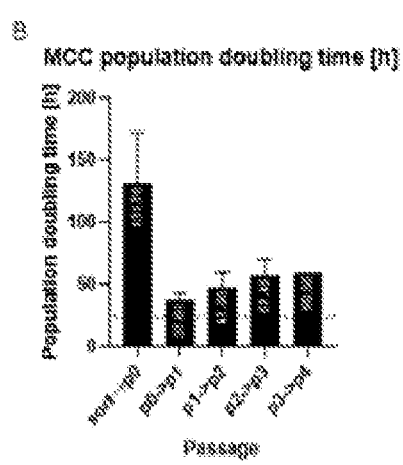
Figure 9:
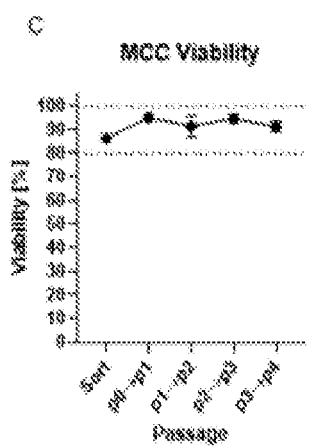
Figure 9:
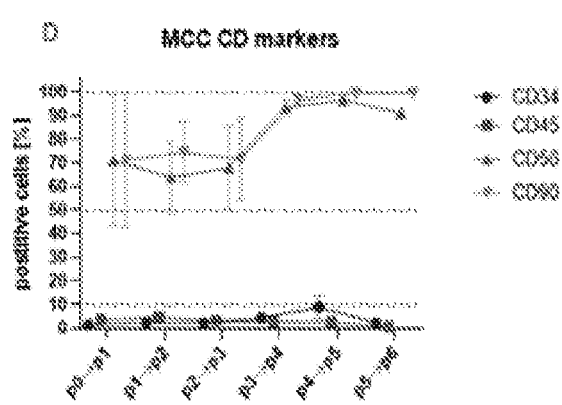

In certain embodiments, myoblasts from the healthy donor or patient with MD, or generated MCC cells, are cryopreserved during the manufacturing process (e.g., depending on the number of cells generated after certain passages). FIGS. 6 and 7 provide exemplary flow charts describing examples of when such cells are cryopreserved.

In general, the main objective of $MB^N$ (normal donor myoblasts) and $MB^{MD}$ (muscle disease patient myoblasts) myoblast culture in vitro is to obtain enough cells to perform Fusion, cell sorting and further expansion of MCC cells up to at least the number of cells sufficient to prepare the ATMP (Advanced Therapy Medicinal Product) with the Patient's dose of MCCs (e.g., about $100 \times 10^6$ cells). However, in certain embodiments, if the cell yield at early passages of cell culture permits, a certain number of both myoblasts and DEC cells are cryopreserved to create a Working Cell Bank (WCB) (see part 13 further below).

In general, since previously cryopreserved myoblasts should undergo at least one passage (or be cultured for about a week) before they are Fused, passage 2 is generally the most appropriate stage for cryopreservation. Passage 2 is the stage at which the yield of myoblasts should generally be sufficient to cryopreserve about a substantial amount of cells (e.g., $2 \times 10^6$ cells) and either perform Fusion or passage the rest of myoblasts for further expansion. It should be remembered that to perform the Fusion it is necessary to achieve a sufficient number of both $MB^N$ and $MB^{DMD}$ cell lines. In certain embodiments, if one of the cell lines proliferates faster, it should undergo a reduction passage to match the other line number. Excess cells, in some embodiments, are subjected to cryopreservation. The cells on Passage 2 can be cryopreserved and then thawed for further culture (e.g., another Fusion) if needed. Similarly, if cell yield makes it possible, a certain number of MCC cells can be cryopreserved, as a potential source of cells for an additional dose of ATMP.

Provided below is a description of the cryopreservation and fusion flowcharts in FIGS. 6 and 7. This description is exemplary. If the cell yield of passage 2 myoblasts (MBP2) is about $\geq 16 \times 10^6$ cells, the number of cells is sufficient to cryopreserve $2 \times 10^6$ cells, perform a Fusion and collect cells for Quality Control. Therefore, about $2 \times 10^6$ cells are cryopreserved, and sample collected for Quality Control. Then, $4\text{-}18.5 \times 10^6$ cells are used for Fusion(s). If the number of cell yield of both $MB^N$ and $MB^{MD}$ is sufficient, more than one Fusion can be performed, each one from at least $4 \times 10^6$ cells of each cell line.

If the cell yield of passage 2 myoblasts (MB P2) is about $12\text{-}16 \times 10^6$ cells, the number of cells is sufficient to cryopreserve $2 \times 10^6$ cells, perform a Fusion and collect cells for Quality Control. Therefore, about $2 \times 10^6$ cells are cryopreserved and samples are collected for Quality Control. The remaining cells are used for Fusion(s). If the number of cell yield of both $MB^N$ and $MB^{MD}$ is sufficient, more than one Fusion should be performed, each one from at least $4 \times 10^6$ cells of each cell line. If the cell yield of passage 2 myoblasts (MB P2) is about $6\text{-}12 \times 10^6$ cells, then about $2 \times 10^6$ cells are cryopreserved. The remaining cells are passaged to passage 3. If the cell yield of passage 2 myoblasts (MB P2) is $<6 \times 10^6$ cells, the cells should be passaged to passage 3.

If the cells were passaged to passage 3 and the yield of passage 3 myoblasts (MB P3) is $\geq 14 \times 10^6$ cells, the number of cells is sufficient to cryopreserve $2 \times 10^6$ cells, perform a Fusion(s) and collect cells for Quality Control. Therefore, about $2\times10^6$ cells are cryopreserved. Samples should be collected for Quality Control. Then, about $4-18.5\times10^6$ cells are used for Fusion(s). If the number of cell yield of both $MB^N$ and $MB^{MD}$ is sufficient, more than one Fusion can be performed, each one from at least $4\times10^6$ cells of each cell line.

If the cells were passaged to passage 3 and the yield of passage 3 myoblasts (MB P3) is about $10-14\times10^6$ cells, then about $2\times10^6$ cells should be collected for Quality Control. Then, about $4-18.5\times10^6$ cells should be used for Fusion(s). If the number of cell yield of both $MB^N$ and $MB^{MD}$ is sufficient, more than one Fusion could be performed, each one from at least $4\times10^6$ cells of each cell line.

If the cells were passaged to passage 3 and the yield of passage 3 myoblasts (MB P3) is $<10\times10^6$ cells, then the cells should be passaged to passage 4. If the cells were passaged to passage 4 and the yield of passage 4 myoblasts (MB P3) is $\geq14\times10^6$ cells, the number of cells is sufficient to perform a Fusion(s) and collect cells for Quality Control. Therefore, samples should be collected for Quality Control. Then, $4-18.5\times10^6$ cells are used for Fusion(s). If the number of cell yield of both $MB^N$ and $MB^{MD}$ is sufficient, more than one Fusion could be performed, each one from at least $4\times10^6$ cells of each cell line.

If the cells were passaged to passage 3 and the yield of passage 4 myoblasts (MB P4) is $10-14\times10^6$ cells, then samples should be collected for Quality Control. Then, $4-18.5\times10^6$ cells are used for Fusion(s). If the number of cell yield of both $MB^N$ and $MB^{DMD}$ is sufficient, more than one Fusion could be performed, each one from at least $4\times10^6$ cells of each cell line.

If the cell yield of passage 3 MCC (MCC P3) is sufficient for the preparation of ATMP with Patient's dose of MCC (e.g., with the additional 10%), the one could perform cryopreservation of $>=5\times10^6$ cells and Quality Control. Samples are collected for Quality Control. Then, $>=5\times10^6$ cells are cryopreserved. Reference sample should be collected, and Final Product should be prepared.

If the cell yield of passage 3 MCC (MCC P3) is sufficient for the preparation of ATMP with Patient's dose of MCC (e.g., with the additional 10%), then samples should be collected for Quality Control. A reference sample should be collected and Final Product should be prepared.

If the cell yield of passage 3 MCC (MCC P3) is insufficient for the preparation of ATMP with Patient's dose of MCC (e.g., with the additional 10%) and Quality Control should be performed. MCC cells should be passaged to passage 4

If the MCC cells were passaged to passage 4 and the yield on passage 4 (MCC P4) is sufficient for the preparation of ATMP with Patient's dose of MCC (e.g., with the additional 10%), cryopreservation of $>=5\times10^6$ cells, Quality Control should be performed. Then, $>=5\times10^6$ cells should be cryopreserved. Reference sample should be collected and Final Product should be prepared.

If the MCC cells were passaged to passage 4 and the yield on passage 4 (MCC P4) is sufficient for the preparation of ATMP with Patient's dose of MCC (e.g., with the additional 10%), samples should be collected for Quality Control. Reference sample should be collected, and Final Product should be prepared.

If the cell yield of passage 4 MCC (MCC P4) is insufficient for the preparation of ATMP with Patient's dose of MCC (e.g., with the additional 10%), quality control should be performed and MCC cells should be passaged to passage 5.

If the MCC cells were passaged to passage 5 and the yield on passage 5 (MCC P5) is sufficient for the preparation of ATMP with Patient's dose of MCC (e.g., with the additional 10%), then samples should be collected for Quality Control. Reference sample should be collected, and Final Product should be prepared.

If the cell yield of passage 5 MCC (MCC P5) is insufficient for the preparation of ATMP with Patient's dose of MCC (e.g., with the additional 10%), Samples should be collected for Quality Control. Based on the results of QC, The Principal Investigator or other medical professional should decide if the Final Product should be prepared or the MCC cells should be passaged or the MCC cell culture should be canceled.

13. Cell Banking

In certain embodiments, the cells described herein may be used for cell banking (e.g., cryopreserved as described above). For example, after expansion, the cells are prepared for fusion as described herein, and the remaining yield for cryopreservation being divided into cryovials, frozen and stored for repository (e.g., in liquid nitrogen vapors at $-196°$ C.). The cryopreservation of both the parental myoblasts and MCC cells may be performed as known in the art. For example, such cryopreservation may be performed according to manufacturer's manual for CryoStor® CS10 as described in the following exemplary protocol.

First, after obtaining a cell suspension, cells are centrifuged to obtain a cell pellet. The supernatant is removed with a pipette, with small amount of medium left to ensure the cell pellet is not disturbed. The cell pellet is resuspended by gently flicking the tube. Cold (2-8° C.) CryoStor® CS10 is added, mixed thoroughly, and the suspension is transferred to a cryovial. Cells are incubated at 2-8° C. for 10 minutes. The cells are cryopreserved using a standard slow rate-controlled cooling protocol (approximately $-1°$ C./minute) or an isopropanol freezing container and stored at liquid nitrogen temperature ($-196°$ C.).

The cells are cryopreserved depending on the available number for the purpose of further re-dosing if necessary. The exemplary flow-charts presented in FIGS. 6 and 7 reflect the decision making on the cryopreservation time points that may be employed in certain embodiments. The cryopreserved cells can serve as Working Cell Banks (WCB) either for parental myoblasts or MCC cells.

In certain embodiments, in the case of parental myoblasts, the decision on cryopreservation is taken at P2 when the number of cells is sufficient to run fusion, quality control and WBC establishment. In some embodiments, the number of cells for cryopreservation is not smaller than $2\times10^6$ cells per mL. If there will be a replication of the required minimum number of cells, the appropriate replicates of cryovials will be prepared.

In case of MCC cells, the similar approach as for the parental myoblasts may be considered. The WCB of parental myoblasts or MCC cells is established in case the trial participant is unable to accept the product on scheduled time-point but the manufacturing process is already ongoing or in case re-dosing schedule is recommended.

14. Exemplary Reagents

With the procedures and protocols described above, the reagents listed in Table 3 may be employed.

TABLE 3

List of reagents that may be used during the manufacturing process

| Reagent | Concentration | Vendor | Grade |
|---|---|---|---|
| DMEM (without phenol red) | 4.5 g/L Glucose<br>4.0 mM L-glutamine<br>1.0 mM sodium pyruvate | HyClone<br>(cat# SH30604.01) | GMP |
| HBSS (without phenol red) | 1.0 g/L Glucose<br>1.26 mM Calcium Chloride ($CaCl_2$)<br>5.33 mM Potassium Chloride (KCl)<br>0.44 mM Potassium Phosphate Monobasic ($KH_2PO_4$)<br>0.50 mM Magnesium Chloride ($MgCl_2$—$6H_2O$)<br>0.41 mM Magnesium Sulfate ($MgSO_4$—$7H_2O$)<br>138 mM Sodium Chloride (NaCl)<br>4 mM Sodium Bicarbonate ($NaHCO_3$)<br>0.30 mM Sodium Phosphate Dibasic ($Na_2HPO_4$) | Biological Industries<br>(cat# 02-016-1A) | GMP (for in vitro use only) |
| DPBS (without phenol red, calcium chloride and magnesium chloride) | 2.67 mM Potassium Chloride (KCl)<br>1.47 mM Potassium Phosphate Monobasic ($KH_2PO_4$)<br>136.9 mM Sodium Chloride (NaCl)<br>8.10 mM Sodium Phosphate Dibasic ($Na_2HPO_4$) | Biological Industries<br>(cat# 02-023-1A) | GMP grade<br>CE marked, QMS ISO 13485: 2016 |
| Human Platelet Lysate (hPL) | n/a | PL-Bioscience (500 ml cat# PLS-500.02-FD; 100 ml cat# PLS-100.02-FD; 50 ml cat# PLS-050.02-FD)<br>Or<br>PL-Bioscience (500 ml cat# PLS-500.03-FDi; 100 ml cat# PLS-100.03-FDi, 50 ml cat# PLS-050.03-FDi) | GMP grade |
| Collagenase | 1 g | Nordmark<br>(cat# N0002779) | GMP, Ph. Eur. (sterility), (for in vitro use only) |
| TrypLE Select | 1× | Gibco (cat# 12563-029) | GMP, (RUO or further manufacturing) |
| L-Alanyl-L-Glutamine | 200 mM | Biological Industries<br>(cat# 03-022-1B) | GMP (RUO or in vitro diagnostics) |
| Antibiotic-Antimycotic | 10,000 units/mL of penicillin, 10,000 μg/mL of streptomycin, and 25 μg/mL of Gibco Amphotericin B (100×) | Gibco<br>(cat# 15240062) | RUO |
| MSC Attachment | 5 ml (100×) | Biological Industries<br>(cat# 05-752-1H) | GMP (for use as ancillary material in manufacturing cell, gene or tissue based products) |
| hBFGF-Recombinant Human FGF basic/FGF2 GMP | 25 μg | BioTechne<br>(cat# 233-GMP-025) | GMP (clinical ex vivo use) |
| PKH26 Diluent C | $1 \times 10^{-3}$M in ethanol | Sigma-Aldrich<br>(cat# MIDI26-1KT) | RUO |
| PKH67 Diluent C | $1 \times 10^{-3}$M in ethanol | Sigma-Aldrich<br>(cat# MIDI67-1KT) | RUO |
| Human Albumin CSL Behring 200 g/l | 200 g/L (96% human albumin, solution for infusion) | CSL Behring GmbH | GMP (registered medicinal product, marketing authorization number in Poland: 22095) |

TABLE 3-continued

List of reagents that may be used during the manufacturing process

| Reagent | Concentration | Vendor | Grade |
| --- | --- | --- | --- |
| Polyethylene glycol (PEG) 4000 (powder) (EMPROVE ® ESSENTIAL Ph Eur) | 5 kg | Merck (cat# 8170065000) | GMP (Ph Eur) |
| Sorting buffer: MACS GMP PBS/MgCl$_2$ Buffer | n/a | Miltenyi Biotec (cat# 170-076-155) | GMP (USP <1043> for ancillary materials, RUO or ex vivo cell culture processing) |
| Sorting buffer: MACS GMP Tytonase | 20× Stock solution | Miltenyi Biotec (cat# 170-076-210) | GMP (USP <1043> for ancillary materials, RUO or ex vivo cell culture processing) |
| CryoSure-DMSO | 99.9% | Wak Chemie Medical GmbH (cat# WAK-DMSO-50) | GMP (Ph. Eur., USP grade) medical device |
| CryoStor CS10 | 10% DMSO | Stem Cell Technologies (cat# 07959; cat# 07931; cat# 07930; cat# 07952) | GMP (Ph. Eur., USP grade) |
| Natrium Chloratum 0.9% Fresenius | 0.9% sodium chloride | Fresenius Kabi Polska Sp. z o.o. | GMP (registered medicinal product, market authorization number in Poland: 02510) |

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

I claim:

1. A method of generating myoblast chimeric cells comprising:
    a) establishing:
        i) a MD (muscle disease) cell culture comprising MD non-passaged myoblast cells derived from a first human subject with a muscle disease (MD), and
        ii) a Donor cell culture comprising non-passaged Donor myoblast cells derived from a second human subject without said MD;
    b) culturing and passaging said MD cell culture, and said Donor cell culture, at least twice and not more than four times, to generate:
        i) a population of 2-4 times passaged MD myoblasts, and
        ii) a population of 2-4 times passaged Donor myoblasts;
    c) combining at least a portion of said population of 2-4 times passaged MD myoblasts, with at least a portion of said population of 2-4 times passaged Donor myoblasts, to generate a cell mixture, and
    d) adding a cell-fusion solution to said cell mixture to generate a cell fusion reaction such that a population of myoblast chimeric cells (MCCs) is generated, wherein each of said MCCs comprises: i) one of said 2-4 times passaged MD myoblasts, and ii) one of said 2-4 times passaged Donor myoblasts.

2. The method of claim 1, wherein said culturing and passaging of said MD cell culture and said Donor cell culture is performed three times, generating a population of 3 times passaged MD myoblasts and a population of 3 times Donor myoblasts, and wherein each of said MCCs comprise one of said 3 times passaged MD myoblasts and one of said 3 times passaged Donor myoblasts.

3. The method of claim 1, wherein said culturing and passaging of MD cell culture is performed three times, and said culturing and passaging of said Donor cell culture is performed four times, generating a population of 3 times passaged MD myoblasts and 4 times Donor myoblasts, and wherein said each of said MCCs comprise one of said 3 times passaged MD myoblasts and one of said 4 times passaged Donor myoblasts.

4. The method of claim 1, wherein said culturing and passaging of MD cell culture is performed four times, and said culturing and passaging of said Donor cell culture is performed three times, generating a population of 4 times passaged MD myoblasts and 3 times Donor myoblasts, and wherein said each of said MCCs comprise one of said 4 times passaged MD myoblasts and one of said 3 times passaged Donor myoblasts.

5. The method of claim 1, further comprising testing at least one of the following: said population of 2-4 times passaged MD myoblasts and said population of 2-4 times passaged Donor myoblasts,
    wherein said testing generates at least one tested cell population, and wherein said tested cell population meets at least one of the following criteria:
        i) less than 10% of said passaged myoblasts express CD34,
        ii) less than 10% of said passaged myoblasts express CD45, iii) greater than 45% of said passaged myoblasts express CD56, and iv) greater than 45% of said passaged myoblasts express CD90.

6. The method of claim 1, wherein said cell-fusion solution comprises polyethylene glycol (PEG) at a concentration of 0.5-1.5 g/ml.

7. The method of claim 1, further comprising: e) culturing and passaging said MCCs at least once and not more than three times, to generate: a population of 1-3 times passaged MCCs.

8. The method of claim 7, wherein said passaging of said MCCs at least once but not more than three times is when, for each passaging, said MCCs are at about 60-80% confluency.

9. The method of claim 1, wherein culturing and passaging said MD cell culture, and said Donor cell culture, at least twice and not more than four times, is performed when such cell cultures are at about 60-80% confluency.

10. The method of claim 1, wherein said muscle disease (MD) of said first subject is a muscular dystrophy.

11. The method of claim 10, wherein said muscular dystrophy is Duchenne muscular dystrophy.

* * * * *